US007959919B2

(12) United States Patent
Bansal

(10) Patent No.: US 7,959,919 B2
(45) Date of Patent: Jun. 14, 2011

(54) METHOD OF INHIBITING FACTOR B-MEDIATED COMPLEMENT ACTIVATION

(75) Inventor: Rekha Bansal, Twinsburg, OH (US)

(73) Assignee: NovelMed Therapeutics, Inc., Cleveland, OH (US)

( * ) Notice: Subject to any disclaimer, the term of this patent is extended or adjusted under 35 U.S.C. 154(b) by 1557 days.

(21) Appl. No.: 10/716,929

(22) Filed: Nov. 19, 2003

(65) Prior Publication Data

US 2005/0107319 A1 May 19, 2005

(51) Int. Cl.
*A61K 39/395* (2006.01)
(52) U.S. Cl. ............... 424/145.1; 424/130.1; 424/141.1
(58) Field of Classification Search ................ None
See application file for complete search history.

(56) References Cited

U.S. PATENT DOCUMENTS 6,333,034 B1 * 12/2001 Gupta-Bansal et al. ... 424/139.1

FOREIGN PATENT DOCUMENTS

WO    WO 00/21559    *    4/2000

OTHER PUBLICATIONS

Harlow, E et al. Antibodies: A Laboratory Manual. [1988] pp. 72-77, 92-97, 128-135, 141-157 and 628-631.*
Owens et al. (Journal of Immunological Methods, 1994, 168:149-165).*
Clardy, C.W. Complement Activation by Whole Endotoxin Is Blocked by a Monoclonal Antibody to Factor B. *Infection and Immunity*, 1994, 62C101, 4599-4555.
Matsumoto, M. et al., Abrogation of the Alternative Complement Pathway by Targeted Deletion of Murine Factor B. *Proc. Natl. Acad. Sci. USA*. 1997, 94, 8720-8725.
Hourcade, D.E. et al. Analysis of the Short Consensus Repeats of Human Complement Factor B by Site-Directed Mutagenesis. *J. Biol. Chem.* 1995, 270 (34), 19716-19722.
Hensley P. et. al. The Effects of Metal Ions and Temperature on the Interaction of Cobra Venom Factor and Human Complement Factor B. *J. Biol. Chem.* 1986, 261 (24), 1103-11044.
Hourcade, D. E. et. al. Mutations of the Type A Domain of Complement Factor B That Promote High-Affinity C36-Binding. *The Journal of Immunology*, 1999, 162, 2906-2911.
Horiuchi, T. et. al. Human Complement Factor B: cDNA Cloning, Nucleotide Sequencing, Phenotypic Conversion. by Site-Directed Mutagenesis and Expression. *Molecular Immunology* 1993, 30 (17), 1587-1592.
Arnstead et al., "Removal of activated complement from shed blood: comparison of high-and low-dilutional haemofiltration". Acta Anaesthesiol Scand. Aug. 1998;42(7):811-5, Abstract Only.
Buono et al., "Influence of C3 Deficiency on Athrerosclerosis". Circulation 2002;105;3025-3031.
Carter et al., "Humanization of an anti-p185$^{HER2}$ antibody for human cancer therapy", Proc. Natl. Acad, Sci USA, vol. 89, pp. 4285-4289, May 1992.

Chenoweth, D.E., Complement activation during cardiopulmonary bypass: evidence for generation of C3a and C5a anaphylatoxins. N Engl J Med, 1981. 304(9): p. 497-503, Abstract Only.
Clardy, C.W., "Complement activation by whole endotoxin is blocked by a monoclonal antibody to factor B." Infect Immun, 1994. 62(10): pp. 4549-4555.
Dahl et al., "MASP-3 and its association with distinct complexes of the Mannan-Binding Lectin Complement Activation Pathway", Immunity, vol. 15, 127-135, Jul. 2001.
Dang, "Relationship between developmental stenosis of cervical spinal canal and spinal cord injury", Zhonghua Wai Ke Za Zhi, Nov. 1992;29(12):724-6, 796, Abstract Only.
Dreyer, WJ, et al. "Neutrophil accumulation in ischemic canine myocardium. Insights into time course distribution, and mechanism of localization during early reperfusion". Circulation 1991; 84;400-411.
Eaton S., et al. "Assay for Plasma Complement Activation by x-ray contrast media". Invest Radiol, 1990. 25(7):p. 789-92, Abstract Only.
Entman, Mark L., et al. "Neutrophil induced oxidative injury of cardiac myocytes", J. Clin. Invest. vol. 90, 1992, p. 1335-1345.
Espinoza, Diego G. et al., "Macrophage Depletion Diminishes Lesion Size and Severity in Experimental Choroidal Neovascularization", Invest Ophthalmol Vis Sci. 2003:44:3586-3592.
Frederick, G.N., L. Truedsson, and A.G. Sjoholm, "New procedure for the detection of complement deficiency by ELISA. Analysis of activation pathways and circumvention of rheumatoid factor influence". J Immunol Methods, 1993: 166(2): p. 263-70, Abstract Only.
Gyoten, M., *Activation of the complement system and cytokine production by radiographic contrast media in vascular endothelial cell in vitro*, Nippon Igaki Hoshasen Gakkai Zasshi Dec. 1998;58(14):811-5, Abstract Only.
Halstensen TS, Brandtzaeg P., *Local Complement activation in inflammatory bowel disease*, Immunol Res. 1991; 10(3-4): 485-92, Abstract Only.
Horiuchi, T., et al., *Human complement factor B: cDNA cloning, nucleotide sequencing, phenotypic conversion by site-directed mutagenesis and expression*. Mol Immunol, 1993. 30(17): p. 1587-92, Abstract Only.

(Continued)

*Primary Examiner* — Sharon Wen
(74) *Attorney, Agent, or Firm* — Tarolli, Sundheim, Covell & Tummino LLP

(57) ABSTRACT

The present invention discloses the method of inhibiting complement activation mediated by factor B inhibitors, that involves: (a) inhibiting factor B binding to properdin-bound C3b; (b) inhibiting the release of Bb; (c) inhibiting the activation of neutrophils, monocytes, platelets, and endothelium; or (d) inhibiting/reducing the formation of PC3bBb, C3a, C5a, and MAC.

The present invention also discloses the novel use of factor B inhibitors in the treatment of various immunological disorders, resulting either primarily from direct immune responses such as rheumatoid arthritis, anaphylactic shock, myasthenia gravis, asthma, Alzheimer's disease, and the like, or secondarily from clinical conditions such as cardiopulmonary bypass inflammation, vascular stenosis and restenosis, burn injury, and the like.

17 Claims, 10 Drawing Sheets

OTHER PUBLICATIONS

Hourcade, D.E., L.M. Wagner, and T.J. Oglesby, *Analysis of the short consensus repeats of human complement factor B by site-directed mutagenesis.* J Biol Chem, 1995. 270(34): p. 19716-22.

Ikeda, Ken et al., *Serum lectin with known structure activates complement through the classical pathway*, Journal of Biological Chemistry. 1987 262(16): p. 7451-7454.

Isaacs, J.D., et al., *Therapy with monoclonal antibodies. An in vivo model for the assessment of therapeutic potential.* J Immunol, 1992. 148(10): p. 3062-71.

Jones HM, et al., *Cardiopulmonary bypass and complement activation. Involvement of classical and alternative pathways.*, Anaesthesia. Jun. 1982;37(6):629-33, Abstract Only.

Jones, Peter T. et al., *Replacing the complementarity-determining regions in a human antibody with those from a mouse*, Nature 321, 522-525, May 29, 1986, Abstract Only.

Kawana S. et al., *Membrane attack complex of complement in Henoch-Schönlein purpura skin and nephristis*, Arch Dermatol Res. 1990;282(3)187-7, Abstract Only.

Kilpatrick, David C., *Mannan-Binding lectin: clinical significance and applications*, Biochimica et Biophysica Acta 1572 (2002) 401-413.

Kitano A., et al., *New treatment of ulcersative colitis with k-76*, Dis Colon Rectum. Jun. 1992;35(6):560-7, Abstract Only.

Kolios G. et al., *Mediators of inflammation: production and implication in inflammatory bowel disease.* Hepatogastroenterology. Sep.-Oct. 1998;45(23):1601-9, Abstract Only.

Lonberg Nils, et al., *Antigen-specific human antibodies from mice comprising four distinct genetic modifications*, Nature 368, 856-859: Apr. 28, 1994, Abstract Only.

Marks, J.D. et al., *By-passing immunization. Human antibodies from v-gene libraries displayed on phage*, J Mol Biol. Dec. 5, 1991;222(3)581-597, Abstract Only.

Moore, F.D., Jr., et al., *The effects of complement activation during cardiopulmonary bypass. Attenuation by hypothermia, heparin, and hemodilution.* Ann Surg, 1988. 208(1): p. 95-103, Abstract Only.

Morgan BP et al., *Measurement of terminal complement complexes in rheumatoid arthritis*, Clin Exp Immunol. Sep. 1998;73(3):473-8, Abstract Only.

Morgan BP, Walport MJ, *Complement deficiency and disease*, Immunol Today. Sep. 1991;12(9):301-6, Abstract Only.

Morrison SL et al., *Chimeric human molecules: mouse antigen-binding domains with human constant region domains*, Proc Natl Acad Sci U S A. Nov. 1984;81(21):6851-5, Abstract Only.

Nakano S, Engel AG, *Myasthenia gravis: quantitative immunocytochemical analysis of inflammatory cells and detection of complement membrane attack complex at the end-plate in 30 patients*, Neurology. Jun. 1993;43(6):1167-72, Abstract Only.

Niculescu F, Rus H. *Complement activation and atherosclerosis*, Mol Immunol. Sep.-Oct. 1999;36(13-14):949-55, Abstract Only.

Pack P. et al., *Improved bivalent miniantibodies, with identical avidity as whole antibodies, produced by high cell density fermentation of Escherichia coli*, Biotechnology (NY). Nov. 1993;11(11):1271-7, Abstract Only.

Pangburn, M.K., R.D. Schreiber, and H.J. Muller-Eberhard, *Formation of the initial C3 convertase of the alternative complement pathway. Acquisition of C3b-like activities by spontaneous hydrolysis of the putative thioester in native C3.* J Exp Med, 1981. 154(3): p. 856-67, Abstract Only.

Polhill, R.B., Jr., K.M. Pruitt, and R.B. Johnston, Jr., *Kinetic assessment of alternative complement pathway activity in a hemolytic system. I. Experimental and mathematical analyses.* J Immunol, 1978. 121(1): p. 363-70.

Ravetch, J.V. and J.P. Kinet, *Fc receptors.* Annu Rev Immunol, 1991. 9: p. 457-92, Abstract Only.

Sandhu JS, *Protein engineering of antibodies*, Crit Rev Biotechnol. 1992;12(5-6):437-62, Abstract Only.

Schafer Hansjorg, et al. *Deposition of the Terminal C5b-9 Complement Complex in infracted areas of human Myocardium*, Journal of Immun. 1986; 137(6); p. 1945-1949.

Schmiedt, Walther et al., *Complement C6 Deficiency Protects Against Diet-Induced Atherosclerosis in Rabbits*, Arterioscler Thromb Vasc Biol. 1998;18:1790-1795.

Schulze, M. et al., *Glomerular C3c localization indicates ongoing immune deposit formation and complement activation in experimental glomerulonephritis*, Am J Pathol. Jan. 1993;142(1):179-87, Abstract Only.

Seifert PS, et al. *Isolation and characterization of a complement-activating lipid extracted from human atherosclerosis lesions*, J Exp Med. Aug. 1, 1990;172(2):547-57, Abstract Only.

Seifert PS, et al., *Generation of Complement anaphylatoxins and C5b-9 by crystalline cholesterol oxidation derivatives depends on hydroxyl group number and position*, Mol Immunol. Dec. 1987;24(12):1303-8, Abstract Only.

Seifert PS, et al. *The complement system in atherosclerosis*, Athrerosclerosis. Oct. 1987;73(2-3):91-104, Abstract Only.

Singer II, et al., *Optimal humanization of 1B4, an anti-CD18 murine monoclonal antibody, is achieved by correct choice of human V-region framework sequences*, J Immunol. Apr. 1, 1993;150(7):2844-57, Abstract Only.

Stevens, John H., et al. *Effects of anti-C5a antibodies on the Adult Respiratory Distress Syndrome in Septic Primates*, 1986. 77: p. 1812-1816.

Tada, T. et al., *Membrane attack complex of complement and 20 kDa homologous restriction factor (CD59) in myocardial infarction*, Virchows Archiv, 1997. 430(4): p. 327-332, Abstract Only.

Takabayashi T., et al., *A new biologic role for C3a and C3a desArg: regulation of TNF-alpha and IL-1 beta synthesis*, J Immunol. May 1, 1996;156(9):3455-60, Abstract Only.

Theil, Steffen et al., *Interaction of C1q abd Mannan-Binding Lectin (MBL) with C1r, c1s, MBL-Associated Serine Proteases 1 and 2, and the MBL-Associated Protein MA919*, J. Immunol 2000. 165:878-887.

Tomooka K., *Serum complement levels in patients with rheumatoid arthritis and vasculitis*, Fukuoka Ilgaku Zasshi. Oct. 1989;80(10):456-66, Abstract Only.

Utley, J.R., *Pathophysiology of cardiopulmonary bypass: current issues.* J Card Surg, 1990. 5(3): p. 177-89, Abstract Only.

van de Winkel, J.G. and P.J. Capel, *Human IgG Fc receptor heterogeneity: molecular aspects and clinical implications.* Immunol Today, 1993. 14(5): p. 215-21, Abstract Only.

Woodruff Trent M., et al., *A Potent Human C5a Receptor Antagonist Protects against disease Pathology in a Rat Model of Inflammatory Bowel Disease*, J. Immunol. 2003. 171:5514-5520.

Yasojima, K. et al., *Complement Components, but not Complement Inhibitors, Are Upregulated in Atherosclerotic Plaques*, Arterioscler. Thromb. Vasc. Biol. 2001;21;1214-1219.

Ames, R.S., et al., *Identification of a selective nonpeptide antagonist of the anaphylatoxin C3a receptor that demonstrates antiinflammatory activity in animal models.* J Immunol, 2001. 166(10): p. 6341-8.

Acioli, J.M., M. Isobe, and S. Kawasaki, "Early Complement System Activation and Neutrophil priming in acute pancreatitis: Participation of trypsin", Surgery 1997. 122(5) pp. 909-917.

Barnum, S.R., et al., "Expression of the complement C3a and C5a are increased in bronchoalveolar lavage fluid after segmental allergen provocation in subjects with asthma". Am J Respir Crit Care Med, 2001. 164(10 Pt 1): 1841-3.

Basta, M., I. Illa, and M.C. Dalakas, "Increased in vitro uptake of the complement C3b in the serum of patients with Guillain-Barre syndrome, myasthenia gravis and dermatomyositis". J Neuroimmunol, 1996. 71(1-2): p. 227-9.

Bellander, B.M., et al., "Complement activation in the human brain after traumatic head injury". J Neutrotrauma, 2001. 18(12): p. 1295-311, Abstract Only.

Belmont, H.M., et al., Complement activation during systematic lupus erythematosus. C3a and C5a anaphylatoxins circulate during exacerbations of disease. Arthritis Rheum, 1986, 29(9); p. 1085-9, Abstract Only.

Bonser, R.S., et al., "Complement activation before, during and after cardiopulmonary bypass". Eur J Cardiothorac Surg, 1990. 4(6): p. 291-6, Abstract Only.

Chenoweth, D.E., "Anaphylatoxin formation in extracorporeal circuits", Complement, 1986. 3(3): p. 152-65, Abstract Only.

Davis, E.A., et al., "Inhibition of neutrophil adhesion and the membrane attack complex of complement synergistically prolongs cardiac xenograft survival", J Heart Lung Transplant, 1995, 14(5): p. 973-80, Abstract Only.

del Balzo, U., M.J. Polley, and R. Levi, "Cardiac anaphylaxis. Complement activation as an amplification system". Circ Res, 1989. 65(3):p. 847-57.

Furman, M.I., et al., *Circulating monocyte-platelet aggregates are an early marker of acute myocardial infarction*. J Am Coll Cardiol, 2001. 38(4): p. 1002-6.

Furman, M.I., et al., *Increased platelet reactivity and circulating monocyte-platelet aggregates in patients with stable coronary artery disease*. J Am Coll Cardiol, 1998. 31(2): p. 352-8.

Gerard, N.P. and C. Gerard, *Complement in allergy and asthma*. Curr Opin Immunol, 2002. 14(6): p. 705-8.

Gillinov, A.M., et al., *Complement inhibition with soluble complement receptor type 1 in cardiopulmonary bypass*. Ann Thorac Surg, 1993. 55(3): p. 619-24, Abstract Only.

Gloor, B., et al., *Predictive value of complement activation fragments C3a and sC5b-9 for development of severe disease in patients with acute pancreatitis*. Scand J Gastroenterol, 2003. 38(10): p. 1078-82, Abstract Only.

Gong, J., et al., *Tubing loops as a model for cardiopulmonary bypass circuits: both the biomaterial and the blood-gas phase interfaces induce complement activation in an in vitro model*. J Clin Immunol, 1996. 16(4): p. 222-9, Abstract Only.

Haeffner-Cavaillon, N., et al., *C3a(C3adesArg) induces production and release of interleukin 1 by cultured human monocytes*. J Immunol, 1987. 139(3): p. 794-9.

Holmes, J.H.t., et al., *Magnitude of the inflammatory response to cardiopulmonary bypass and its relation to adverse clinical outcomes*. Inflamm Res, 2002. 51(12): p. 579-86, Abstract Only.

Hopkins, P., et al., *Increased levels of plasma anaphylatoxins in systemic lupus erythematosus predict flares of the disease and may elicit vascular injury in lupus cerebritis*. Arthritis Rheum, 1988. 31(5): p. 632-41, Abstract Only.

Horigome, I., et al., *Terminal complement complex in plasma from patients with systemic lupus erythematosus and other glomerular diseases*. Clin Exp Immunol, 1987. 70(2): p. 417-24.

Howard, R.J., et al., *Effects of cardiopulmonary bypass on pulmonary leukostasis and complement activation*. Arch Surg, 1988. 123(12): p. 1496-501, Abstract Only.

Humbles, A.A., et al., *A role for the C3a anaphylatoxin receptor in the effector phase of asthma*. Nature, 2000. 406(6799): p. 998-1001.

Johnson, L.V., et al., *Complement activation and inflammatory processes in Drusen formation and age related macular degeneration*. Exp Eye Res, 2001. 73(6): p. 887-96, Abstract Only.

Kaczorowski, S.L., et al., *Effect of soluble complement receptor-1 on neutrophil accumulation after traumatic brain injury in rats*. J Cereb Blood Flow Metab, 1995. 15(5): p. 860-4, Abstract Only.

Kirschfink, M., et al., [*Significance of the complement system for xenotransplantation: strategies for therapeutic intervention*]. Zentralbl Chir, 1998. 123(7): p. 793-7, Abstract Only.

Krug, N., et al., *Complement factors C3a and C5a are increased in bronchoalveolar lavage fluid after segmental allergen provocation in subjects with asthma*. Am J Respir Crit Care Med, 2001. 164(10 Pt 1): p. 1841-3.

Langlois, P.F. and M.S. Gawryl, *Detection of the terminal complement complex in patient plasma following acute myocardial infarction*. Atherosclerosis, 1988. 70(1-2): p. 95-105, Abstract Only.

Lien, Y.H., L.W. Lai, and A.L. Silva, *Pathogenesis of renal ischemia/reperfusion injury: lessons from knockout mice*. Life Sci, 2003. 74(5): p. 543-52.

Lin F. et al., *Decay-Accelerating Factor Deficiency Increases Susceptibility to Dextran Sulfate Sodium-Induced Colitis: Role for Complement in Inflammatory Bowel Disease*, Journal of Immunology 2004, 172:3836-3841.

Mead, R.J., et al., *The membrane attack complex of complement causes severe demyelination associated with acute axonal injury*. J Immunol, 2002. 168(1): p. 458-65, Abstract Only.

Meuer, S., et al., *Platelet-serotonin release by C3a and C5a: two independent pathways of activation*. J Immunol, 1981. 126(4): p. 1506-9, Abstract Only.

Mohr, R., et al., *The hemostatic effect of transfusing fresh whole blood versus platelet concentrates after cardiac operations*. J Thorac Cardiovasc Surg, 1988. 96(4): p. 530-4, Abstract Only.

Mullins, R.F., N. Aptsiauri, and G.S. Hageman, *Structure and composition of drusen associated with glomerulonephritis: implications for the role of complement activation in drusen biogenesis*. Eye, 2001. 15(Pt 3): p. 390-5, Abstract Only.

Nataf, S., et al., *Attenuation of experimental autoimmune demyelination in complement-deficient mice*. J Immunol, 2000. 165(10): p. 5867-73, Abstract Only.

Pruitt, S.K., et al., *The effect of soluble complement receptor type 1 on hyperacute rejection of porcine xenografts*. Transplantation, 1994. 57(3): p. 363-70, Abstract Only.

Rinder, C.S., et al., *Cardiopulmonary bypass induces leukocyte-platelet adhesion*. Blood, 1992. 79(5): p. 1201-5, Abstract Only.

Rinder, C.S., et al., *Role of C3 cleavage in monocyte activation during extracorporeal circulation*. Circulation, 1999. 100(5): p. 553-8, Abstract Only.

Rinder, C.S., et al., *Blockade of C5a and C5b-9 generation inhibits leukocyte and platelet activation during extracorporeal circulation*. J Clin Invest, 1995. 96(3): p. 1564-72.

Roxvall, L., A. Bengtson, and M. Heideman, *Anaphylatoxin generation in acute pancreatitis*. J Surg Res, 1989. 47(2): p. 138-43, Abstract Only.

Roxvall, L.I., L.A. Bengtson, and J.M. Heideman, *Anaphylatoxins and terminal complement complexes in pancreatitis. Evidence of complement activation in plasma and ascites fluid of patients with acute pancreatitis*. Arch Surg, 1990. 125(7): p. 918-21, Abstract Only.

Saatvedt, K., et al., *Complement activation and release of tumour necrosis factor alpha, interleukin-2, interleukin-6 and soluble tumour necrosis factor and interleukin-2 receptors during and after cardiopulmonary bypass in children*. Scand J Clin Lab Invest, 1995. 55(1): p. 79-86, Abstract Only.

Schmid, E., et al., *Requirement for C5a in lung vascular injury following thermal trauma to rat skin*. Shock, 1997. 8(2): p. 119-24, Abstract Only.

Simpson, P.J., et al., *Reduction of experimental canine myocardial reperfusion injury by a monoclonal antibody (anti-Mo1, anti-CD11b) that inhibits leukocyte adhesion*. J Clin Invest, 1988, 81(2): p. 624-9, Abstract Only.

Stahel, P.F., M.C. Morganti-Kossmann, and T. Kossmann, *The role of the complement system in traumatic brain injury*. Brain Res Brain Res Rev, 1998. 27(3): p. 243-56, Abstract Only.

Stahl, G.L., et al., *Role for the alternative complement pathway in ischemia/reperfusion injury*. Am J Pathol, 2003. 162(2): p. 449-55, Abstract Only.

Thurman, J.M., et al., *Lack of a functional alternative complement pathway ameliorates ischemic acute renal failure in mice*. J Immunol, 2003. 170(3): p. 1517-23, Abstract Only.

Torzewski, J., et al., *Complement-induced release of monocyte chemotactic protein-1 from human smooth muscle cells. A possible initiating event in atherosclerotic lesion formation*. Arterioscler Thromb Vasc Biol, 1996. 16(5): p. 673-7, Abstract Only.

Undar, A., et al., *Novel anti-factor D monoclonal antibody inhibits complement and leukocyte activation in a baboon model of cardiopulmonary bypass*. Ann Thorac Surg, 2002. 74(2): p. 355-62; discussion 362, Abstract Only.

van Beek, J., K. Elward, and P. Gasque, *Activation of complement in the central nervous system: roles in neurodegeneration and neuroprotection*. Ann N Y Acad Sci, 2003. 992: p. 56-71, Abstract Only.

Vedeler, C.A., et al., *Soluble complement receptor type 1 in serum and cerebrospinal fluid of patients with Guillain-Barre syndrome and multiple sclerosis*. J Neuroimmunol, 1996. 67(1): p. 17-20, Abstract Only.

Vickers, J., et al., *Measurement of platelet activation and adhesion to leukocytes during haemodialysis*. Platelets, 1998. 9(3-4): p. 261-4, Abstract Only.

Wan, K.C., et al., *A longitudinal study of C3, C3d and factor Ba in burn patients in Hong Kong Chinese*. Burns, 1998. 24(3): p. 241-4.

Wang, Y., et al., *Anti-C5 monoclonal antibody therapy prevents collagen-induced arthritis and ameliorates established disease.* Proc Natl Acad Sci U S A, 1995. 92(19): p. 8955-9.

Ware, L.B. and M.A. Matthay, *The acute respiratory distress syndrome.* N Engl J Med, 2000. 342(18): p. 1334-49.

Yasuda, M., et al., *The complement system in ischemic heart disease.* Circulation, 1990. 81(1): p. 156-63, Abstract Only.

Zhou, W., et al., *Predominant role for C5b-9 in renal ischemia/reperfusion injury.* J Clin Invest, 2000. 105(10): p. 1363-71.

Ahlgren, E., et al., *Neurocognitive impairment and driving performance after coronary artery bypass surgery.* Eur J Cardiothorac Surg, 2003. 23(3): p. 334-40, Abstract Only.

Cecic, I., J. Sun, and M. Korbelik, *Role of complement anaphylatoxin C3a in photodynamic therapy-elicited engagement of host neutrophils and other immune cells.* Photochem Photobiol, 2006. 82(2): p. 558-62, Abstract Only.

Keith, J.R., et al., *Assessing postoperative cognitive change after cardiopulmonary bypass surgery.* Neuropsychology, 2002. 16(3): p. 411-21.

Levy, J.H. and K.A. Tanaka, *Inflammatory response to cardiopulmonary bypass.* Ann Thorac Surg, 2003. 75(2): p. S715-20.

Mahanna, E.P., et al., *Defining neuropsychological dysfunction after coronary artery bypass grafting.* Ann Thorac Surg, 1996. 61(5): p. 1342-7.

Neumann, E., et al., *Local production of complement proteins in rheumatoid arthritis synovium.* Arthritis Rheum, 2002. 46(4): p. 934-45, Abstract Only.

Newman, M.F., Kirchner J.L., Phillips-Bute B., *Longitudinal assessment of neurocognitive function after cornary artery bypass surgery.* N Engl J Med, 2001. 344: p. 395-402.

Rinder, C.S., et al., *Selective blockade of membrane attack complex formation during simulated extracorporeal circulation inhibits platelet but not leukocyte activation.* J Thorac Cardiovasc Surg, 1999. 118(3): p. 460-6.

Seines, O.A. and G.M. McKhann, *Neurocognitive complications after coronary artery bypass surgery.* Ann Neurol, 2005. 57(5): p. 615-21, Abstract Only.

\* cited by examiner

METHOD OF INHIBITING FACTOR B-MEDIATED COMPLEMENT ACTIVATION

FIELD OF THE INVENTION

The present invention relates to complement activation. Particularly, the present invention relates to the method for inhibiting complement activation via the alternative pathway. More particularly, the present invention relates to novel method of inhibiting the binding of factor B to properdin-bound C3b, for inhibiting the formation of complement activation products, and for inhibiting the complement-mediated activation of neutrophils, monocytes, and platelets; and to the treatment of various immunological and clinical disorders resulting from complement activation.

BACKGROUND OF THE INVENTION

It is to be noted that throughout this application various publications are referenced by Arabic numerals within brackets. Full citations for these publications are listed at the end of the specification. The disclosures of these publications are hereby incorporated by reference in their entireties into this application in order to more fully describe the state of the art to which this invention pertains.

Complement can be activated through either of two distinct enzymatic cascades referred to as the classical and alternative pathways. The classical pathway is usually triggered by antibody bound to a foreign particle, and thus requires prior exposure to that particle for the generation of specific antibody. There are four plasma proteins involved in the classical pathway: C1, C2, C3 and C4. The interaction of C1 with the Fc regions of IgG or IgM in immune complexes activates a C1 protease that can cleave plasma protein C4, resulting in the C4a and C4b fragments. C4b can bind another plasma protein, C2. The resulting species, C4b2, is cleaved by the C1 protease to form the classical pathway C3 convertase, C4b2a. Addition of the C3 cleavage product, C3b, to C3 convertase leads to the formation of the classical pathway C5 convertase, C4b2a3b [1, 2].

In contrast to the classical pathway, the alternative pathway is spontaneously triggered by foreign or other artificial (plastic/glass) or abnormal surfaces (bacteria, yeast, virally infected cells, or damaged tissue), and is therefore capable of an immediate response to an invading organism. There are four plasma proteins directly involved in the alternative pathway: C3, factor B, factor D, and factor P (referred to as 'properdin'). C3 is converted into C3b and C3a by C3 convertase. Properdin in human blood binds C3b to form P-C3b complex. Factor B binds both free C3b and P-C3b, and both factor B-bound complexes are cleaved by factor D to form a new set of complexes, C3bBb and C3bBbP, which possess C3 convertase activity. The resulting convertase cleaves C3, producing the C3b fragment, which can covalently attach to the target and then interact with factors B and D to form the alternative pathway C3 convertase [3, 4].

The alternative pathway C3 convertase is stabilized by C3b bound properdin. Since the substrate for the alternative pathway C3 convertase is C3, C3 is therefore both a component and a product of the reaction. As the C3 convertase generates increasing amounts of C3b, an amplification loop is established. Furthermore, the classical pathway can also generate C3b that C3b can bind factor B and thereby engage the alternative pathway. This allows more C3b to deposit on a target. Both the classical and alternative pathways converge at C3, which is cleaved to form C3b and C3a. C3a is a potent anaphylatoxin and has been implicated in the pathogenesis of a variety of clinical indications. C3a activates neutrophils, monocytes, platelets, mastcells, and T lymphocytes. C3a has been shown to be important for the induction of paw edema in an adjuvant-induced arthritis model [5, 6].

Addition of C3b to C3 convertase generates C5 convertase, which cleaves C5 to produce C5b and C5a. C5a is the most potent anaphylatoxin that causes alterations in smooth muscle, in vascular tone, and in vascular permeability. It is also a powerful chemotaxin and an activator of neutrophils, monocytes, platelets, endothelial cells, and T lymphocytes. C5a-mediated cellular activation can significantly amplify inflammatory responses by inducing the release of additional inflammatory mediators, including cytokines, hydrolytic enzymes, arachadonic acid metabolites and reactive oxygen species.

The cleavage of Cb produces C5b and C5a. C5b combines with C6, C7, C8, and C9 to form the C5b-9 complex at the surface of the target cell. C5b is also known as the membrane attack complex (MAC). There is now strong evidence that MAC may play an important role in inflammation in addition to its role as a lytic pore-forming complex. C5b-9 is also known to mediate platelet activation. Activated platelets express CD62P (P selectin). P-selectin mediates platelet-monocyte binding, and such binding triggers the release of tissue factor from monocytes. One result of such conjugate formation is the removal of platelets from the circulation, a phenomenon that can contribute to the development of thrombocytopenia.

While complement activation provides a valuable first-line defense against potential pathogens, the activities of complement that promote a protective inflammatory response can also represent a potential threat to the host. For example, C3a and C5a anaphylatoxins recruit and activate neutrophils, monocytes and platelets. These activated cells are indiscriminate in their release of destructive enzymes and may cause organ damage. In addition, complement activation may cause the deposition of lytic complement components resulting in host cell lysis. Currently, there are no approved drugs exist that can inhibit the damages caused by the complement pathway. Based upon the available clinical data, it appears that in most acute injury settings, complement activation is mediated predominantly by the alternative pathway [7]. Therefore, developing suitable methods that inhibit only this pathway without completely obviating the immune defense capabilities would be highly desirable. This would leave the classical pathway intact to handle immune complex processing and to aid in host defense against infection.

Factor B plays a key role in the alternative pathway since it provides the catalytic subunit, Bb, for the C3 convertase, PC3bBb. Since factor B is specific to and is an essential component of the alternative pathway, it presents an attractive target for specifically inhibiting this pathway. Factor B by itself is a zymogen with no known catalytic activity, but after binding PC3b, factor B is cleaved by factor D. Inhibition of factor B results in selective inhibition of factor binding to properdin-bound C3b, thereby leading to the inhibition of formation of C3a, C5a and C5b-9, which are responsible for many deleterious effects mentioned previously. Based on this, it should be possible to develop specific inhibitors or inhibition methods that will (a) prevent factor B binding to properdin-bound C3b, and/or (b) suppress factor B cleavage that prevent Bb generation. Monoclonal antibodies to human factor B have been prepared and tested for their in vitro ability to prevent factor B binding to C3b alone [8]. These antibodies have been tested in endotoxin (LPS) assay and shown to be specific for only gram negative oligosaccharides with relevance to sepsis. Other anti-factor B monoclonal antibodies, although, showed high affinity binding to factor B, stabilized the alternative pathway convertase. The blocking monoclonal antibody inhibited factor B binding to C3b as demonstrated by the inhibition of C3a generation. Surprisingly, none of the prior art publications or patents neither disclose other agents such as peptides, peptidomimetic, oligonucleotides, or any small organic molecules; nor do they suggests the use of factor B inhibitors for the treatment of pathological conditions other than sepsis [8].

SUMMARY OF THE INVENTION

Accordingly, the invention discloses a novel method of inhibiting complement activation by inhibiting the activity of factor B that is responsible for the formation PC3bB or PC3bBb complex. Factor B inhibitors molecule comprise a whole, fragmented anti-factor B antibody; peptides; oligonucleotides; peptitomimetics; or any small organic molecules having a binding region specific to factor B. Antibody fragments can be $F_{ab}$, $F_{(ab)2}$, $F_v$, or single chain $F_v$. The antibody may be monoclonal, polyclonal, chimeric, or DeImmunized. The inhibitor molecule of the present invention should prevent factor B binding to Properdin-bound C3b, inhibit the assembly of C3 convertase (PC3bBb); or prevent the cleavage of factor B into Bb. Peptidomimetics according to the present invention are those molecules that share a common epitope with or function in the similar manner as that of factor B antibody. Likewise, small molecules of present invention comprises compounds haviang molecular weight is less than 2000 Daltons, but typically less that 700 Daltons, and sharing a common epitope with and function in the same manner as factor B antibody. The term 'small molecule' generally implies that they are not recognized by body's immune system. Peptidomimetics or small molecule inhibitors may either bind to factor B, or to properdin at their respective sites of interaction.

The present invention also discloses the use of factor B inhibitors for the treatment of several disease conditions involving complement activation [9-18]. These include, but are not limited to the treatment and prevention of post cardiopulmonary bypass complications; myocardial infarction; ischemia/reperfusion injury; stroke; acute respiratory distress syndrome (ARDS); sepsis; burn injury; inflammation associated with cardiopulmonary bypass and hemodialysis; plasmapheresis; plateletpheresis; leukophereses; extracorporeal; membrane oxygenation (ECMO); heparin-induced extracorporeal LDL precipitation (HELP); radiographic contrast media induced allergic response; transplant rejection; and other inflammatory conditions and autoimmune/immune complex diseases such as multiple sclerosis, myasthemia gravis, pancreatitis, rheumatoid arthritis, Alzheimer's disease, asthma, thermal injury, anaphylactic shock, bowel inflammation, urticaria, angioedema, vasculitis, glomerularnephritis, and Sjogren's syndrome, lupus erythromatosus, and glomerular nephritis.

BRIEF DESCRIPTION OF THE DRAWINGS

Brief Description of the Drawings

Figure 1:
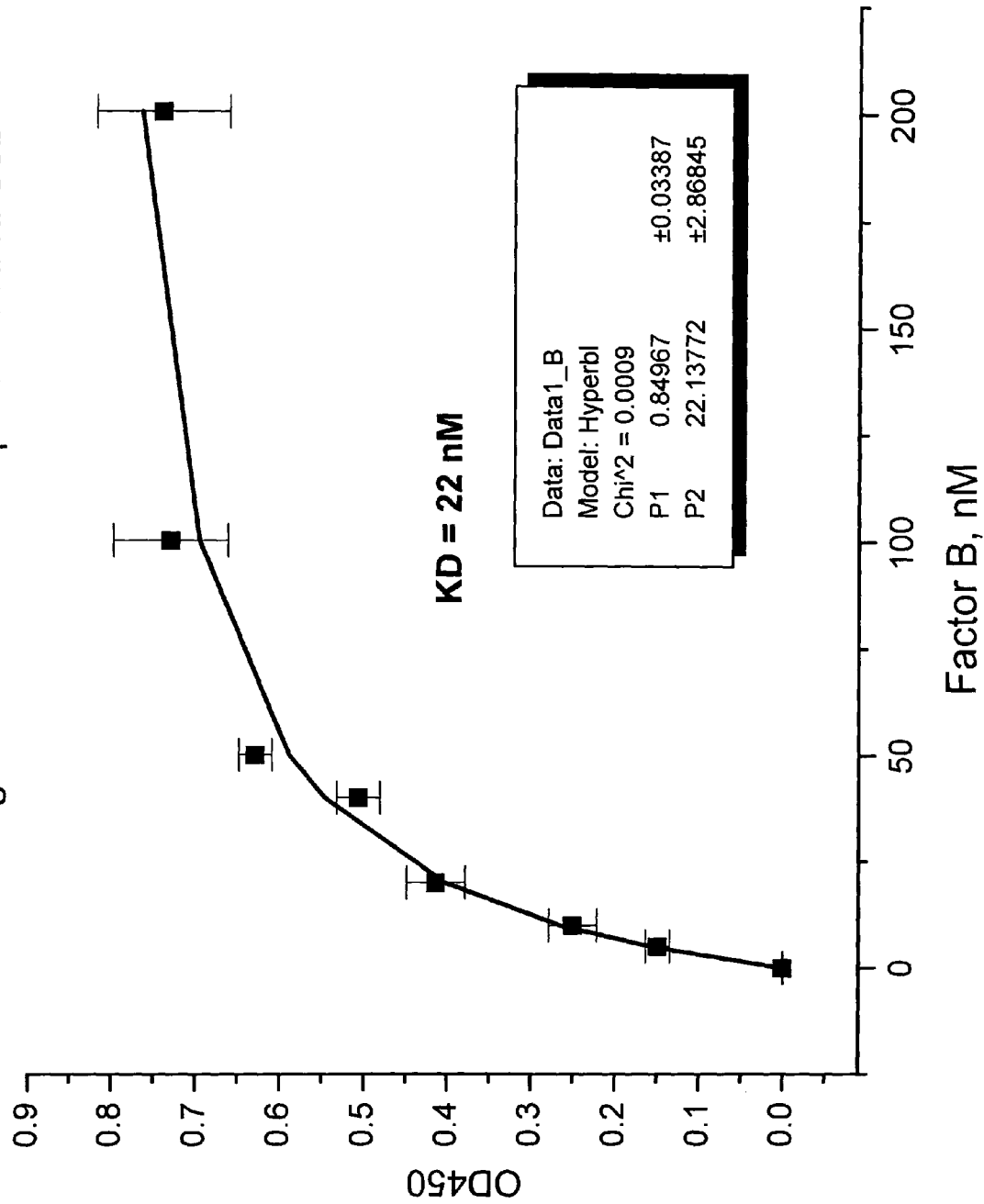

FIG. 1: Solid phase assay demonstrating the binding of human factor B to properdin bound C3b. The vertical (Y) axis represents the reactivity of the factor B with properdin-bound C3b, and the horizontal (X) axis represents the concentration of factor B.

Figure 2:
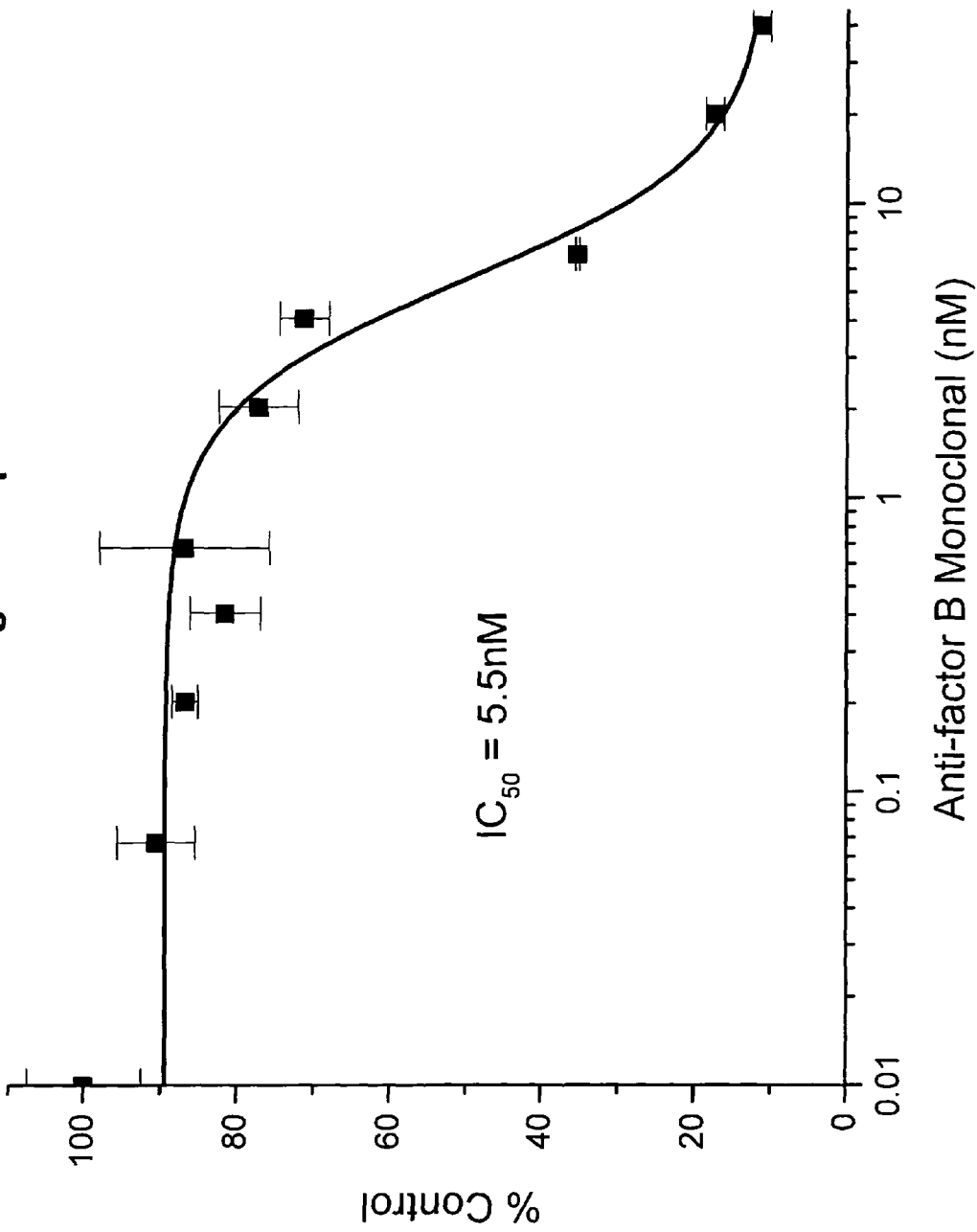

FIG. 2: Dose-dependent inhibition of factor B binding to properdin-bound C3b using an anti-factor B monoclonal antibody. The Y axis represents the inhibition of factor B binding, and the X axis represents the concentration of anti-factor B antibody.

Figure 3:
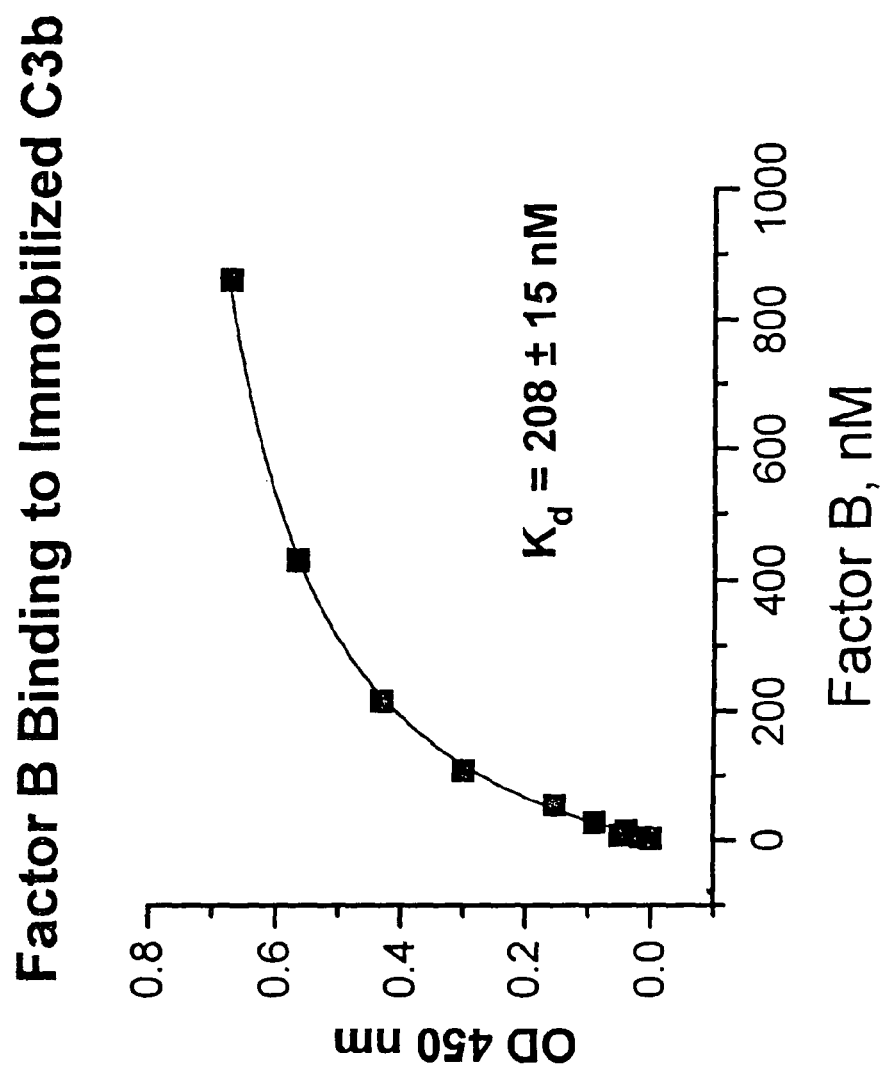

FIG. 3: Solid phase assay demonstrating the binding of human factor B to C3b. The vertical (Y) axis represents the reactivity of the factor B with C3b, and the horizontal (X) axis represents the concentration of factor B.

Figure 4:
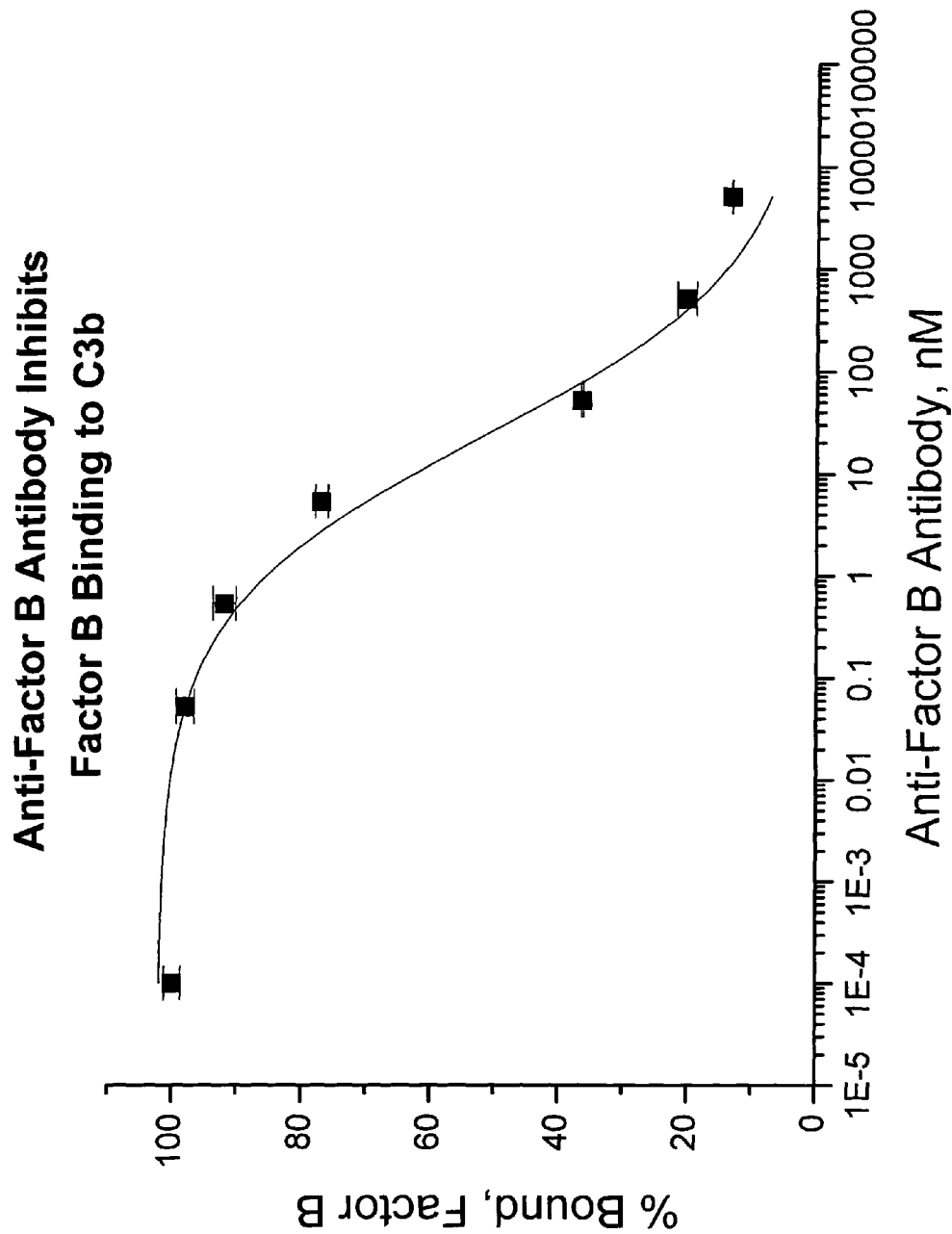

FIG. 4: Dose-dependent inhibition of factor B binding to C3b using an anti-factor B monoclonal antibody. The Y axis represents the inhibition of factor B binding, and the X axis represents the concentration of anti-factor B antibody.

Figure 5:
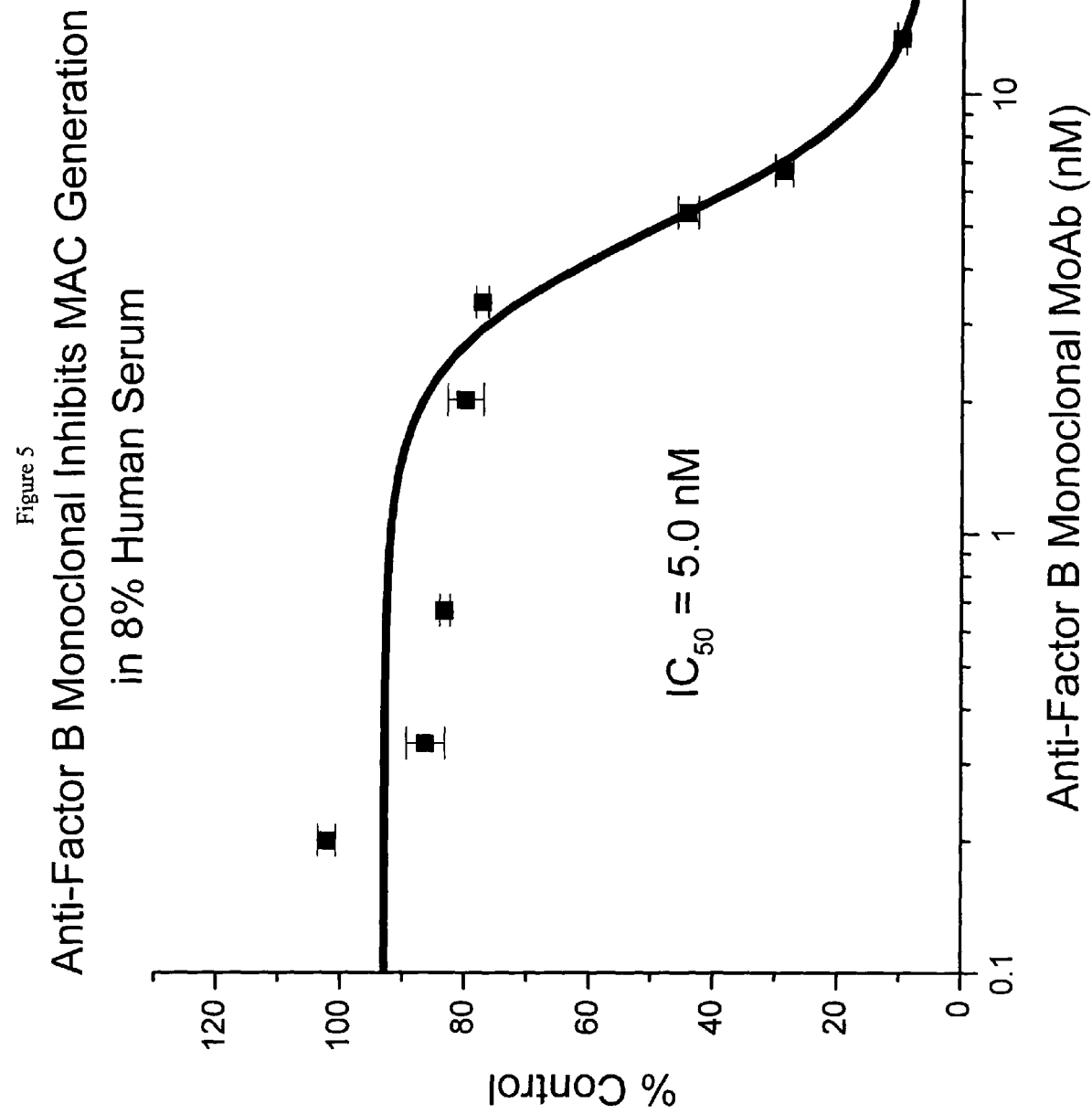

FIG. 5: Assay of MAC deposition on LPS coated surface. In the assay, anti factor B antibody in 8% normal human serum is incubated with LPS coated surface for 45 minutes at 37° C. Following the incubation, MAC deposited on LPS coated surface is quantified using anti-MAC antibody. As shown in the figure, Y axis represents the level of C5b-9 and the X axis represents the concentration of anti-factor B antibody.

Figure 6:
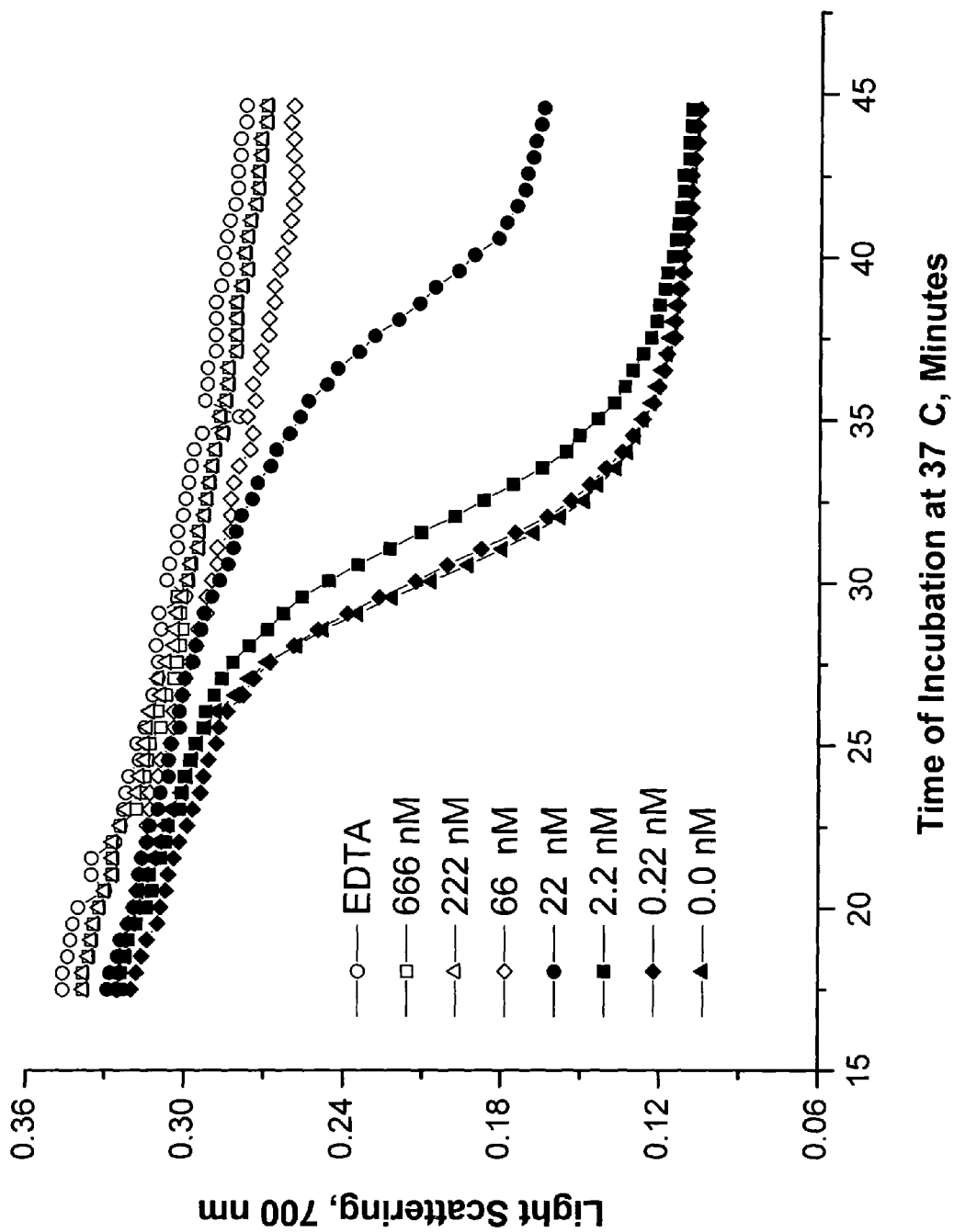

FIG. 6: Alternative pathway dependent rabbit erythrocyte hemolytic assay demonstrating anti-factor B monoclonal antibody inhibition of complement activity associated with human serum. The blocking antibody in 8% normal human serum was incubated with rabbit erythrocytes. As a result of complement activation erythrocytes lyse and cause a decrease in the light scattering. As shown in the figure, the Y axis represents light scattering at 700 nm and the X axis represents the incubation time at 37° C. Anti-factor B antibody inhibits rRBC hemolysis in a progressive manner.

Figure 7:
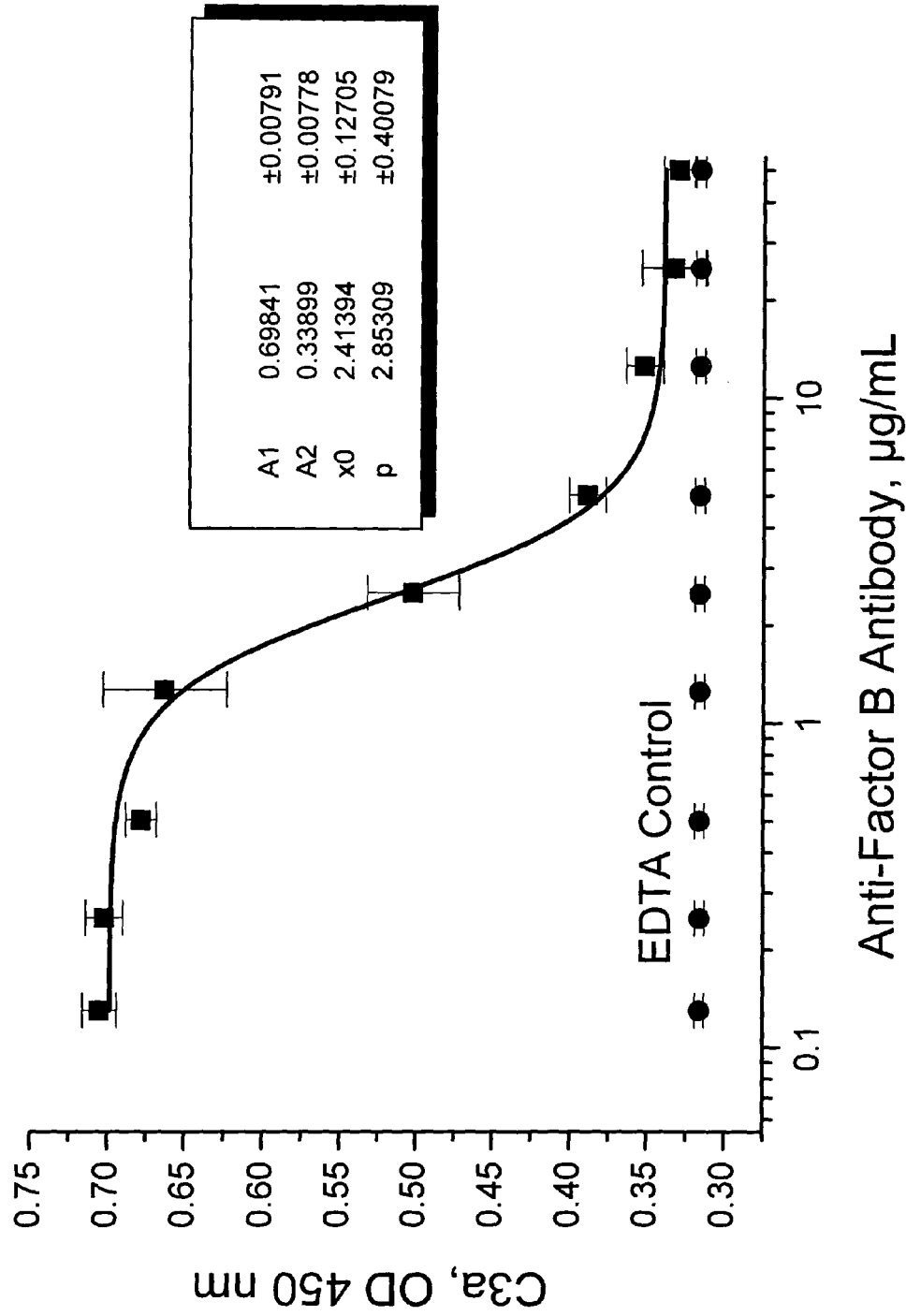

FIG. 7: Assay of levels of complement component C3a in human serum demonstrating that the generation of complement component C3a in human serum is inhibited by the addition of an anti-factor B monoclonal antibody to such human serum. In the assay, anti factor B antibody in 8% normal human serum is incubated with LPS coated surface for 45 minutes at 37° C. Following the incubation, human serum is removed and an aliquot was tested for C3a levels. As shown in the figure, Y axis represents the level of C3a and the X axis represents the concentration of anti-factor B antibody.

Assay of levels of complement component C3b in human serum demonstrating that the generation of complement component C3b in human serum is inhibited by the addition of an anti-factor B monoclonal antibody to such human serum. In the assay, anti factor B antibody in 8% normal human serum is incubated with LPS coated surface for 45 minutes at 37° C. Following the incubation, C3b attached to LPS coating is measured. As shown in the figure, y axis represents the level of C3b and the x axis represents the concentration of anti-factor B antibody.

Assay of levels of complement component C5b-9 in human serum demonstrates that the generation of C5b-9 complex (MAC) in human serum is inhibited by the addition of an anti-factor B monoclonal antibody. In the assay, anti factor B antibody in 8% normal human serum is incubated with LPS coated surface for 45 minutes at 37° C. Following the incubation, human serum is removed and an aliquot was tested for sC5b-9 levels. As shown in the figure, Y axis represents the level of C5b-9 and the X axis represents the concentration of anti-factor B antibody.

Figure 8:
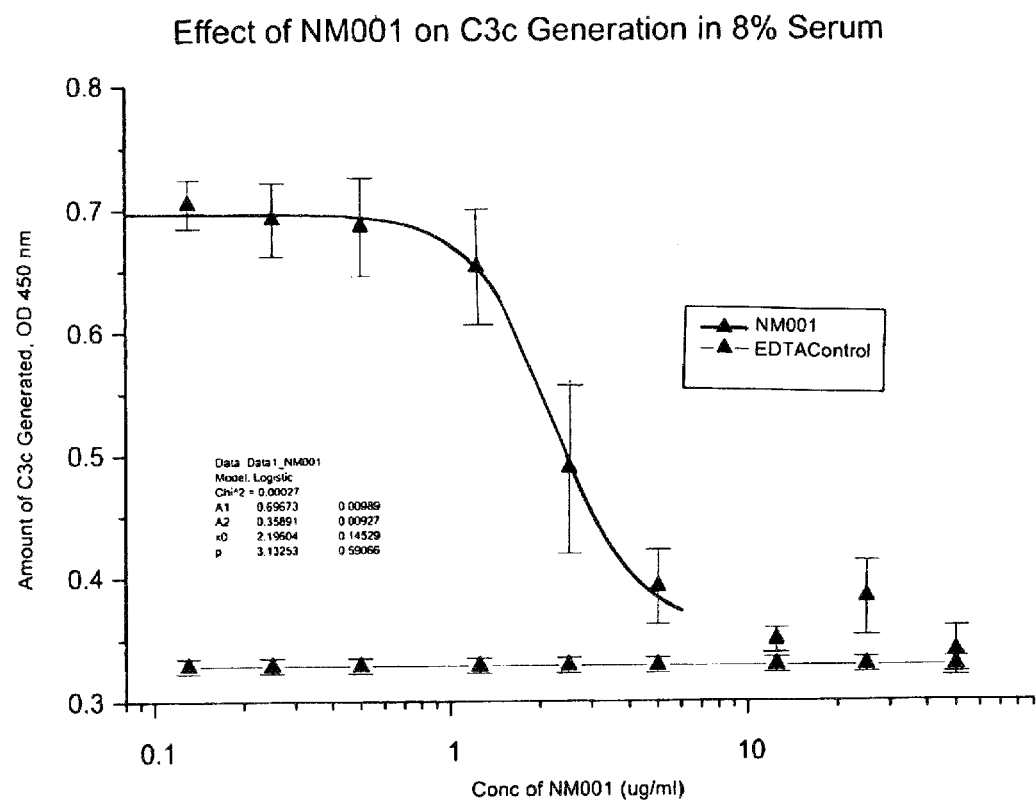

FIG. 8: Assay of levels of complement components C3a, C5a, and C5b-9 demonstrating that the generation of such complement components in human blood is inhibited by the addition of an F(ab)$_2$ fragment of anti-factor B monoclonal antibody to such human blood. A sample of heparinized human whole blood is incubated at 37° C. for 1 hour. As a result of complement activation, complement byproducts such as C3a, C5a, and sMAC (C5b-9) are formed. The figure shows the inhibition of the formation of alternative pathway-dependent complement and activation products in whole blood. Complement activation was measured by the levels of C3a, C5a, and MAC. The Y axis in each case shows the level of activated component and the X axis shows treatment condition.

Figure 9:
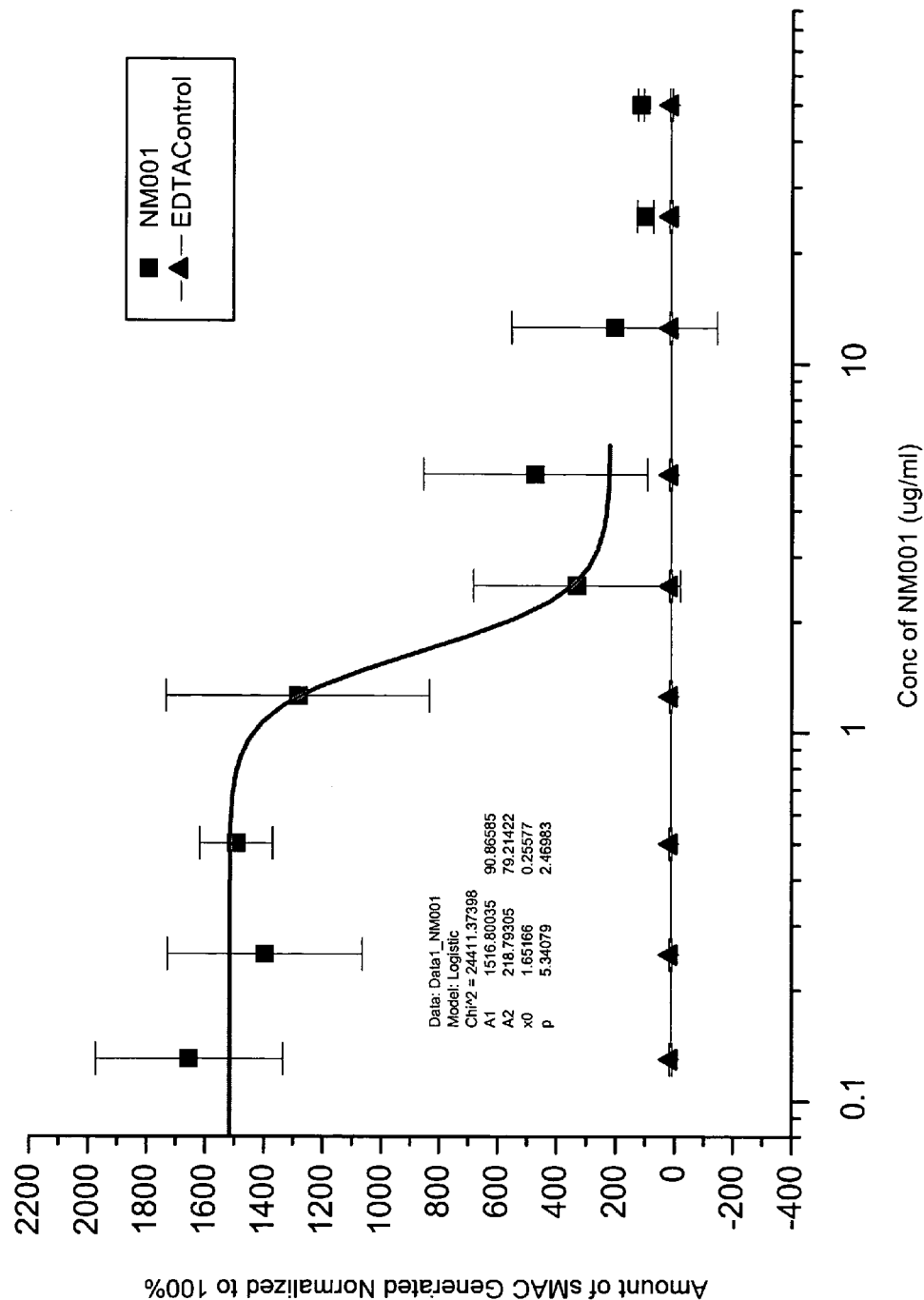

FIG. 9: Flow cytometric analysis of levels of CD11b on neutrophils and monocytes and CD62P on platelets. An $F_{(ab)2}$ fragment of anti-factor B monoclonal antibody was added to whole human blood, following which the samples were analyzed using flow cytometry. The results show that the anti-factor B antibody inhibits activation of neutrophils, monocytes and platelets in human blood in a tubing loop model of extracorporeal circulation. The figure shows the inhibition of CD11b on neutrophils and monocytes and CD62P on platelets in whole blood recirculating in a tubing loop model at 37° C. The Y axis shows CD62P expression and the X axis shows the corresponding treatment conditions.

Figure 10:
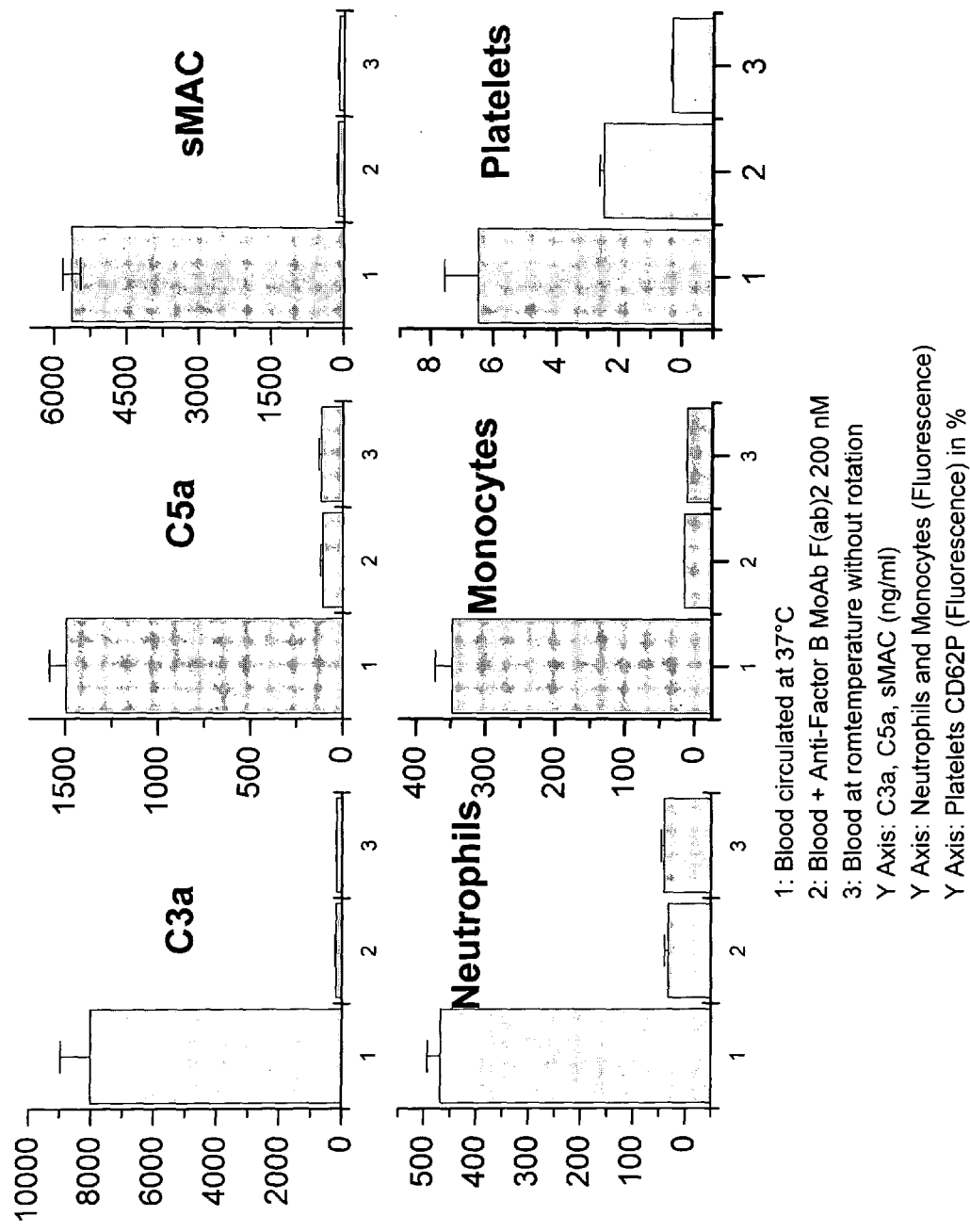

FIG. 10 illustrates graphs showing the levels of C3a, C5a, sMAC, neutrophils, monocytes, and platelets in: (1) blood circulated at 37 degrees C.; (2) blood circulated at 37 degrees C. administered anti-factor B MoAb F(ab)2 at 200 nM; and (3) blood at room temperature without rotation.

DETAILED DESCRIPTION OF THE INVENTION

The present invention discloses the method of inhibiting complement activation mediated by factor B inhibitors that involves: (a) inhibiting factor B binding to properdin-bound C3b; (b) inhibiting the release of Bb, an alternative pathway specific complement by product; (c) inhibiting the activation of neutrophils, monocytes, platelets, and endothelium; or (d) inhibiting/reducing the formation of PC3bBb, C3a, C5a, and MAC in a number of clinical conditions where the disease pathology is complement-mediated. The present invention also discloses the novel use of factor B inhibitors in the treatment of many immunological disorders, either direct ones such as anaphylactic shock, rheumatoid arthritis, and the like, or secondary ones resulting from primary clinical conditions such as cardiopulmonary bypass inflammation, burn injury, and the like. The diseases treated by factor B inhibitors include, but are not limited to myocardial infarction, ischemia/reperfusion injury; vascular stenosis or post-angioplasty restenosis; stroke; acute respiratory distress syndrome (ARDS); sepsis; burn injury; cardiopulmonary bypass inflammation; extracorporeal circulation such as hemodialysis, plasmapheresis, plateletpheresis, leukopheresis, extracorporeal membrane oxygenation (ECMO), or heparin-induced extracorporeal LDL precipitation (HELP); allergic response to the use of radiographic contrast media; transplant rejection; other inflammatory conditions and autoimmune/immune complex diseases that are closely associated with complement activation such as multiple sclerosis, myasthenia gravis, pancreatitis, rheumatoid arthritis, Alzheimer's disease, asthma, thermal injury, anaphylactic shock, bowel inflammation, urticaria, angioedema, vasculitis, and Sjogren's syndrome, lupus erythrosatosus, membranous nephritis, and dermatomysitis.

A preferred embodiment of invention relates to the method of inhibiting complement activation with whole or fragmented, chimeric, deimmunized, humanized, or human or recombinant anti-factor B antibodies.

Another preferred embodiment of the invention relates to the method of inhibiting complement activation with peptides, peptidomimetics, or small molecules.

Another preferred embodiment of the invention relates to the treatment of cardiovascular conditions such as cardiopulmonary bypass inflammation; myocardial infarction; ischemia/reperfusion injury; vasculitis; or vascular stenosis and restenosis.

Another preferred embodiment of the invention relates to the treatment of neurological conditions such as Alzheimer's disease, myasthenia gravis, stroke, and multiple sclerosis.

Another preferred embodiment of the invention relates to the treatment of lupus erythromatosus, rheumatoid arthritis, dermatomysitis, and transplant rejection.

Anti-factor AFB-MoAbs can be prepared by standard methods well known in the art. For example, rodents (e.g. mice, rats, hamsters, and guinea pigs) can be immunized either with native factor B purified from human plasma or urine or with recombinant factor B or its fragments expressed by either eukaryotic or prokaryotic systems. Other animals can also be used for immunization, e.g. non-human primates, transgenic mice expressing human immunoglobulins, and severe combined immunodeficient mice transplanted with human B-lymphocytes. Hybridoma can be generated by conventional procedures well known in the art by fusing B lymphocytes from the immunized animals with myeloma cells (e.g. Sp2/0 and NS0). In addition, anti-factor B antibodies can be generated by screening of recombinant single-chain $F_v$ or $F_{ab}$ libraries from human B lymphocytes in phage-display systems. The specificity of the MoAbs to human factor B can be tested by enzyme linked immunosorbent assay (ELISA).

It would be evident to the one skilled in the art that in vitro studies of complement are representative of and predictive of the in vivo state of the complement system. By way of example, the use of in vitro ELISA (enzyme-linked immunosorbent assay) procedures to detect factor B associated with lipopolysaccharide (LPS) is a "simple, rapid and reliable method for the assessment of complement function particularly the detection of complement deficiency states" [19]. Thus, the in vitro technique can be used in vivo with the same likelihood of success in detecting alternative complement pathway activation in disease states. Furthermore, the standard rabbit erythrocyte hemolysis assay (described in Example 4), which assay is used to measure alternative complement pathway activity, is accepted in the art as being the "most convenient assay for the activity of the human alternative pathway" [20].

The compounds of the present invention can be administered in the pure form, as a pharmaceutically acceptable salt derived from inorganic or organic acids and bases, or as a pharmaceutically 'prodrug.' The pharmaceutical composition may also contain physiologically tolerable diluents, carriers, adjuvants, and the like. The phrase "pharmaceutically acceptable" means those formulations which are, within the scope of sound medical judgment, suitable for use in contact with the tissues of humans and animals without undue toxicity, irritation, allergic response and the like, and are commensurate with a reasonable benefit/risk ratio. Pharmaceutically acceptable salts are well-known in the art, and are described by Berge et al. [21], incorporated herein by reference. Representative salts include, but are not limited to acetate, adipate, alginate, citrate, aspartate, benzoate, benzenesulfonate, chloride, bromide, bisulfate, butyrate, camphorate, camphor sulfonate, gluconate, glycerophosphate, hemisulfate, heptanoate, hexanoate, fumarate, maleate, succinate, oxalate, citrate, hydrochloride, hydrobromide, hydroiodide, lactate, maleate, nicotinate, 2-hydroxyethansulfonate (isothionate), methane sulfonate, 2-naphthalene sulfonate, oxalate, palmitoate, pectinate, persulfate, 3-phenylpropionate, picrate, pivalate, propionate, tartrate, phosphate, glutamate, bicarbonate, p-toluenesulfonate, undecanoate, lithium, sodium, potassium, calcium, magnesium, aluminum, ammonium, tetramethyl ammonium, tetraethylammonium, methylammonium, dimethylammonium, trimethylammonium, triethylammonium, diethylammonium, and ethylammonium, and the like.

The pharmaceutical compositions of this invention can be administered to humans and other mammals enterally or parenterally in a solid, liquid, or vapor form. Enteral route includes, oral, rectal, toipical, buccal, and vaginal administration. Parenteral route intravenous, intramuscular, intraperitoneal, intrasternal, and subcutaneous injection or infusion. The compositions can also be delivered through a catheter for local delivery at a target site, via an intracoronary stent (a tubular device composed of a fine wire mesh), or via a biodegradable polymer.

The active compound is mixed under sterile conditions with a pharmaceutically acceptable carrier along with any needed preservatives, exipients, buffers, or propellants. Opthalmic formulations, eye ointments, powders and solutions are also contemplated as being within the scope of this invention. Actual dosage levels of the active ingredients in the pharmaceutical formulation can be varied so as to achieve the desired therapeutic response for a particular patient. The selected dosage level will depend upon the activity of the particular compound, the route of administration, the severity of the condition being treated, and prior medical history of the patient being treated. However, it is within the skill of the art to start doses of the compound at levels lower than required to achieve the desired therapeutic effect and to increase it gradually until optimal therapeutic effect is achieved. The total daily dose of the compounds of this invention administered to a human or lower animal may range from about 0.0001 to about 1000 mg/kg/day. For purposes of oral administration, more preferable doses can be in the range from about 0.001 to about 5 mg/kg/day. If desired, the effective daily dose can be divided into multiple doses for purposes of administration; consequently, single dose compositions may contain such amounts or submultiples thereof to make up the daily dose.

The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated, the severity of the disorder; activity of the specific compound employed; the specific composition employed, age, body weight, general health, sex, diet of the patient; the time of administration, route of administration, and rate of excretion of the specific compound employed, and the duration of the treatment. The compounds of the present invention may also be administered in combination with other drugs if medically necessary.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof. These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Prolonged absorption of the injectable pharmaceutical form can be brought about by the use of agents delaying absorption, for example, aluminum monostearate and gelatin. Proper fluidity can be maintained, for example, by the use of coating materials such as lecithin, by the maintenance of the required particle size in the case of dispersions, and by the use of surfactants. In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Dosage forms for topical administration include powders, sprays, ointments and inhalants. Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol, and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

The present invention also provides pharmaceutical compositions that comprise compounds of the present invention formulated together with one or more non-toxic pharmaceutically acceptable carriers. Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together. Methods to form liposomes are known in the art [22], incorporated herein by reference.

The compounds of the present invention can also be administered to a patient in the form of pharmaceutically acceptable 'prodrugs.' The term "pharmaceutically acceptable prodrugs" as used herein represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood. A thorough discussion is provided by Higuchi and Stella [23], incorporated herein by reference.

The Examples which follow are presented to describe preferred embodiments and utilities of the invention and are not meant to limit the invention unless otherwise stated in the claims appended hereto. The description is intended as a non-limiting illustration, since many variations will become apparent to those skilled in the art in view thereof. It is intended that all such variation within the scope and spirit of the appended claims be embraced thereby. Changes can be made in the composition, operation, and arrangement of the method of the present invention described herein without departing from the concept and scope of the invention as defined in the claims.

Example 1

Binding of Factor B to Properdin-Bound C3b

Polystyrene microtiter plates were coated with human C3b (0.5 μg/50 μL per well) (Calbiochem, San Diego, Calif.) in phosphate buffered saline (PBS), (5 mM diethyl barbiturate, 120 mM NaCl, 5 mM $MgCl_2$, 5 mM EGTA) overnight at 4° C. After aspirating the C3b solution, wells were blocked with PBS containing 1% bovine serum albumin (BSA) (Sigma Chemical Company, St. Louis, Mo., Cat. No. A7888) for 2 hours at room temperature. Wells without C3b coating served as background controls. Aliquots of human properdin 4 nM in blocking solution were added and plates were allowed to sit for 2 hours to the C3b coated wells to allow properdin binding to C3b. This method would allow the properdin-C3b complex formation. The plate was rinsed with PBS and aliquots of human factor B (or factor B) (Advanced Research Technology, San Diego, Calif.) at varying concentrations in blocking solution were added to the wells. Following 2-hour incubation at room temperature, the wells were extensively rinsed with VBS.

Factor B bound to properdin-bound C3b was detected by the addition of mouse monoclonal anti-human factor B antibody (detection antibody) (Quidel, San Diego, Calif., anti-human factor B monoclonal) at 1:1000 dilution in blocking solution, which was allowed to incubate for 1 hour at room temperature. After washing the plates with VBS, a peroxidase-conjugated goat anti-mouse antibody (1:1000 dilution in blocking solution) (Sigma Chemical Company) was added and allowed to incubate for 1 hour. The plate was again rinsed thoroughly with VBS, and 100 μL of 3,3',5,5'-tetramethyl benzidine (TMB) substrate (Kirkegaard & Perry Laboratories, Gaithersburg, Md., Cat. No. A50-65-00) was added. After incubation for 10 minutes at 25° C., the reaction of TMB was quenched by the addition of 100 μL of phosphoric acid, and the plate was read at 450 nm in a microplate reader (e.g., SPECTRA MAX 250, Molecular Devices, Sunnyvale, Calif.). The estimated $K_d$ of factor B binding to C3b was based on the concentration of factor B at 50% maximal binding (Microcal Origin Program).

As shown in FIG. 1, human factor B binds to Properdin-bound C3b, which has been immobilized onto microtiter plate wells. The apparent binding constant from these data, defined as the concentration of factor B needed to reach half-maximal binding, is approximately 22 nM. The comparison of FIGS. 1 to 4 shows the role of properdin in increasing the affinity of factor B to C3b.

The ability of anti-factor B monoclonal antibodies to inhibit the binding of factor B to Properdin bound C3b was also evaluated. Anti-factor B monoclonal antibody was added to a fixed concentration of factor B in blocking solution. This reaction mixture was incubated with properdin-bound C3b. As shown in FIG. 2 factor B binding to properdin bound C3b is inhibited by the factor B monoclonal antibodies in a dose-dependent fashion at a concentration of about 5 nM.

Factor B bound to properdin-C3b complex was detected by the addition of mouse monoclonal anti-human factor B antibody (detection antibody) (Quidel, San Diego, Calif.) at 1:1000 dilution in blocking solution, which was allowed to incubate for 1 hour at room temperature. After washing the plates with PBS, a peroxidase-conjugated goat anti-mouse antibody (1:1000 dilution in blocking solution) (Sigma Chemical Company) was added and allowed to incubate for 1 hour. The plate was again rinsed thoroughly with PBS, and 100 μL of 3,3',5,5'-tetramethyl benzidine (TMB) substrate (Kirkegaard & Perry Laboratories, Gaithersburg, Md., Cat. No. A50-65-00) was added. After incubation for 10 minutes at 25° C., the reaction of TMB was quenched by the addition of 100 μL of phosphoric acid, and the plate was read at 450 nm in a microplate reader (e.g., SPECTRA MAX 250, Molecular Devices, Sunnyvale, Calif.). The estimated $K_d$ of factor B binding to P-C3b (22 nM) was based on the concentration of factor B at 50% maximal binding (Microcal Origin Program).

As shown in FIG. 1, human factor B binds to properdin bound C3b, which has been immobilized onto microtiter plate wells. The apparent binding constant from these data, defined as the concentration of factor B needed to reach half-maximal binding, is approximately 22 nM.

Example 2

Binding of Factor B to C3b

Polystyrene microtiter plates were coated with human C3b (0.5 μg/50 μL per well) (Calbiochem, San Diego, Calif.) in veronal buffered saline (VBS): (5 mM diethyl barbiturate, 120 mM NaCl, 5 mM $MgCl_2$, 5 mM EGTA) overnight at 4° C. After aspirating the C3b solution, wells were blocked with VBS containing 0.5% human serum albumin (HSA) (Sigma Chemical Company, St. Louis, Mo., Cat. No. A9511) for 2 hours at room temperature. Wells without C3b coating served as background controls. Aliquots of human factor B (Advanced Research Technology, San Diego, Calif.) at varying concentrations in blocking solution were added to the wells. Following 2-hour incubation at room temperature, the wells were extensively rinsed with VBS. C3b-bound B was detected by the addition of mouse monoclonal anti-human factor B antibody (detection antibody) at 1:1000 dilution in blocking solution, which was allowed to incubate for 1 hour at room temperature. After washing the plates with VBS, a peroxidase-conjugated goat anti-mouse antibody (1:1000 dilution in blocking solution) (Sigma Chemical Company) was added and allowed to incubate for 1 hour. The plate was again rinsed thoroughly with VBS, and 100 μL of 3,3',5,5'-tetramethyl benzidine (TMB) substrate (Kirkegaard & Perry Laboratories, Gaithersburg, Md.) was added. After incubation for 10 minutes at 25° C., the reaction of TMB was quenched by the addition of 100 μL of phosphoric acid, and the plate was read at 450 nm in a microplate reader (e.g., SPECTRA MAX 250, Molecular Devices, Sunnyvale, Calif.). The estimated $K_d$ of factor B binding to properdin-bound C3b was based on the concentration of factor B at 50% maximal binding (Microcal Origin Program).

As shown in FIG. 3, human factor B binds to C3b, which has been immobilized onto microtiter plate wells. The apparent binding constant from these data, defined as the concentration of factor B needed to reach half-maximal binding, is approximately 208 nM. We have evaluated the ability of anti-factor B monoclonal antibodies to inhibit the binding of factor B to C3b. Anti-factor B monoclonal antibody was added to a fixed concentration of factor B in blocking solution. This reaction mixture was incubated with C3b. As shown in FIG. 4, factor B binding to C3b is inhibited by the factor B monoclonal antibodies in a dose-dependent fashion.

Example 3

Alternative Pathway

Dependent MAC Assay

The binding and inhibition data above reveal that the factor B monoclonal antibody prevents the binding of factor B to properdin-bound C3b. Since factor B is the critical component of the C3 convertase, it was of interest to us to determine whether the factor B antibody might appreciably affect the terminal aspects of the alternative complement cascade. The final end product of this pathway is the C5b-9 membrane-attack complex (MAC). To analyze the effects of the factor B antibody on MAC formation via the alternative pathway, an assay was utilized in which bacterial LPS was used as a substrate to initiate the alternative complement pathway cascade.

Previous studies have demonstrated that lipopolysaccharide (LPS) from Salmonella Typhosa (S. Typhosa) (Sigma Chemical Company, Cat. No. 6386) serves as a potent substrate for complement alternative pathway activation [19]. Microtiter wells were coated with LPS (2 μg/50 μL per well) in VBS overnight at 4° C. Uncoated wells served as background controls. After aspirating the LPS solution, wells were treated with blocking solution and incubated with various concentrations of normal human serum. Following a 3-hour incubation at 37° C., deposited MAC was detected with mouse anti-human soluble C5b-9 monoclonal antibody (Quidel, Cat. No. A239) using standard ELISA methodologies essentially as described in the Examples above. The effect of the blocking antibody on the MAC formation was evaluated by adding various concentrations of blocking antibody to a fixed concentration of serum (6% in blocking solution). The amount of inhibition of soluble C5b-9 formation was determined using the antibody detection system described in the Examples above.

The formation of MAC in this assay could be completely prevented by the addition of the factor B monoclonal antibody, as seen in FIG. 5 These data indicate that factor B is in fact necessary for progression of the cascade.

Example 4

Alternative Pathway

Dependent Hemolysis

To confirm and extend these results, the factor B antibody was examined in another assay of the alternative pathway. Rabbit erythrocytes initiate the alternative complement cascade, and the resulting formation of MAC causes lysis of these cells. If the factor B antibody is capable of complete inhibition of the alternative pathway, then addition of the reagent to rabbit erythrocytes bathed in human serum should prevent cellular lysis. This can be assayed by examining the light scattering caused by intact red blood cells; lysed cells do not diffract light, and there is a consequent reduction in scattered light. It is well established that rabbit erythrocytes specifically activate the complement alternative pathway, with a resulting lysis of the cells by the C5b-9 complex [20]. Normal human serum, at various concentrations in Gelatin Veronal Buffer (GVB) (Advanced Research Technology) with 5 mM $MgCl_2$ and 10 mM EGTA, was incubated at 37° C. with a fixed number of rabbit erythrocytes (Advanced Research Technology). A progressive decrease in light scatter (due to lysis of intact cells) was measured at 700 nm as a function of time in a temperature-controlled ELISA plate reader. To determine the ability of blocking antibody to inhibit hemolysis of rabbit erythrocytes, various concentrations of the blocking antibody were added to a fixed concentration of normal human serum (8%) and the assay was performed as described above. The data were recorded and analyzed with a Spectra-Max plate reader and software.

As shown in FIG. 6, addition of serum in the absence of factor B antibody resulted in lysis of the cells and a dramatic reduction in light scattering. Addition of increasing concentrations of the antibody caused a decrement in erythrocyte lysis, with 66 nM antibody completely blocking MAC-mediated cellular destruction. These results confirm that monoclonal antibodies that bind and block factor B interaction with properdin-bound C3b are potent reagents that can completely abrogate the effects of the alternative complement pathway.

Example 5

Inhibition of C3a C3b and MAC Production Via Alternative Pathway in Human Serum

This experiment shows that the generation of complement components C3a, C3b, and MAC in human serum is inhibited by the addition of anti-factor B monoclonal antibody to such human serum. Wells of microtiter plates are coated with LPS 2 µg/50 µl in PBS (Lipopolysaccharide from Salmonella Typhosa). The wells were incubated with 1% BSA in PBS to block the unoccupied sites on the plate. Normal human serum (8%) with and without anti-factor B monoclonal antibody was incubated in the wells. The plate was warmed to 37° C. to allow complement activation to occur. Following the incubation, human serum is removed and an aliquots were tested for C3a and sMAC using standard ELISA levels. Substrate-bound C3b was detected with anti-C3c antibody (Accurate Biochemicals). As shown in the Figures, Y axis represents the level of C3a (FIG. 7), C3b (FIG. 8), and sMAC (FIG. 9) and the X axis represents the concentration of anti-factor B antibody. The data shows that anti-factor B monoclonal antibody inhibits C3a, C3b, and sMAC generation in 8% normal human serum.

Example 6

Cardiopulmonary Bypass

Tubing Loop Model

To test the effect of a blocking anti-factor B monoclonal antibody fragment ($F(ab)_2$, as described in Examples 2-5 above, on inhibition of complement activation in cardiopulmonary bypass (CPB), a tubing loop model of CPB as described by Gong, J. R. et al. [24] was utilized. $(F(ab)_2$ lacks the $F_c$ region which is known to cause $F_c$ receptor response. Whole blood from a healthy donor was collected into a 7-ml vacutainer tube (Becton Dickinson, San Jose, Calif.) containing 20 U of heparin/mL of blood. Polyethylene tubing like that used during CPB (PE 330; I.D., 2.92 mm; O.D., 3.73 mm; Clay Adams, N.J.) was filled with 0.5 mL of the heparinized human blood and closed into a loop with a short piece of silicon tubing. Heparinized blood containing 20 mM EDTA (which inactivates complement) served as a background control. Sample and control tubing loops were rotated vertically in a water bath for 1 hour at 37° C. After incubation, blood samples were transferred into 1.7 ml siliconized eppendorf tubes which contained 0.5 M EDTA to give a final EDTA concentration of 20 mM. The samples were centrifuged (4000.× g for 5 minutes at 4° C.) and the plasma were collected. The plasma samples were diluted to 10% with sample diluent buffer and the amounts of C3a as well as soluble MAC (sMAC) were determined using ELISA assay kits following the manufacturer's instructions (Quidel, Catalog Nos. A015 for C3a and A009 for C5b-9/MAC).

For complement inhibition studies, various concentrations (200 nM) of blocking anti-factor B monoclonal antibody described in Examples 2-5 were added to the heparinized blood immediately before circulation for 1 hour at 37° C. After circulation/rotation in a 37° C. water bath for 1 hour, aliquots were analyzed for soluble C3a, C5a, and sMAC as described above using ELISA assay kits (Quidel).

Using this simplified CPB paradigm in which standard CPB tubing was partially filled with fresh human blood, leaving an air-blood interface and where the tubing is joined end-to-end with a silicon sleeve to form a loop, such that this blood-filled loop is rotated in a heated water bath (37° C.) to simulate the movement of blood through a bypass circuit, there is marked activation of complement during the rotation of the blood in the tubing. Importantly, the blocking antihuman properdin antibody causes significant inhibition of this complement activation. This can be seen in FIG. 10, where the formation of soluble membrane-attack complex (sMAC) in the loop model is nearly completely inhibited by 200 nM anti-factor B antibody. Likewise, the same amount of antibody causes a significant reduction in C3a and C5a formation (FIG. 10).

This is the first demonstration of the effectiveness of factor B agent that selectively inhibits alternative pathway activation in a model of CPB.

Example 7

Blocking Agents

Screening and Identification

Agents, which selectively block the formation of complement activation products via the alternative complement pathway, including preferred anti-human factor B antibodies, may be obtained and then screened, identified and selected as taught herein, for their ability to substantially or completely block the formation or production of alternative complement pathway-dependent activation products, including in conditions involving initiation of the classical complement pathway.

Five commercially available anti-human factor B monoclonal antibodies were screened for blocking activity: (a) Accurate anti-human Factor B (clone 008-04); (b) Accurate anti-human Factor B (clone HAV005-$O_2$); (c) Accurate anti human Factor B (clone HAV005-03); (d) Accurate anti-human factor B(KSK002-001); and (e) Quidel anti-human Factor B. However, only the Quidel monoclonal antibody completely blocked alternative pathway complement activation, as detected by complete inhibition of C3a, C5a, C3b, and MAC formation.

According to the present invention, agents are therefore effectively screened for essentially complete, partial or no blocking activity in one or more assays as described herein, including blocking of factor B binding to properdin-bound C3b, inhibition of C3 convertase formation, blocking of alternative pathway-dependent C3a, C3b, C5a, and MAC formation, blocking of alternative pathway-dependent hemolysis, blocking of alternative pathway-dependent C3a formation, or blocking of one or more markers of alternative pathway-dependent cell activation, including markers of neutrophil activation (CD11b), monocyte activation (CD11b), platelet activation (e.g., P-selection/CD62P), platelet-leukocyte adhesion and endothelial cell activation. Agents may be further screened for lack of activation of Fc gamma receptors by the method described by Hulett et al. incorporated herein by reference in its entirety [25].

REFERENCES

1. Liszewski, et al. The Complement System. In *Fundamental Immunology, Third Edition*, pp. 917-939. W. E. Paul (Ed.). Raven Press: New York.
2. Pangburn. Alternative Pathway of Complement. *Meth. In Enzymology* 1988, 162, 639-653.
3. Hourcade D. E., Wagner, L. M., and Oglesby T. J. Analysis of the Short Consensus Repeats of Human Complement Factor B by Site Directed Mutagenesis. *J. Biol. Chem.* 1995, 270, 19716-19722.
4. Horiuchi, T., Kim Sunghee, Matsumoto, M., Watababe I., Fujita, S., and Volanakis, J. Human Complement Factor B: cDNA Cloning, Nucleotide Sequencing, Phenotype Conversion by Site Directed Mutagenesis and Expression. *Mol. Immunol.* 1993, 30, 1587-1592.
5. Wang, et al. Anti-C5 monoclonal antibody therapy prevents collagen-induced arthritis and ameliorates established disease. *Proc. Natl. Acad. Sci. USA* 1995, 92, 8955-8959.
6. Morgan, et al. Measurement of terminal complement complexes in rheumatoid arthritis. *Clin. Exp. Immunol.* 1988, 73, 473-478.
7. Morgan, et al. Complement deficiency and disease. *Immunology Today* 1991, 12, 301-306.
8. Clardy, C. W. et al. Complement Activation by Whole Endotoxin is Blocked by a Monoclonal Antibody to Factor B. *Infect. and Immun.* 1994, 62, 4549-4555.
9. Schafer, et al. Deposition of the Terminal C5b-9 Complement Complex in Infarcted Areas of Human Myocardium. *J. Immunol.* 1986, 137, 1945-1949.
10. Moore, et al. The Effects of Complement Activation during Cardiopulmonary Bypass. *Ann. Surg.* 1988, 208(1), 95-103.
11. Jones, et al. Cardiopulmonary bypass and complement activation. *Anaesthesia* 1982, 37, 629-633.
12. Kilgore, et al. The complement system in myocardial ischaemia/reperfusion injury. *Cardiovascular Res.* 1994, 28, 437-444.
13. Rinder, et al. Blockade of C5a and C5b-9 Generation Inhibits Leukocyte and Platelet Activation during Extracorporeal Circulation. *J. Clin. Invest.* 1995, 96, 1564-1572.
14. Hsu, et al. The Alternative Pathway Mediates Complement Activation in Reperfusion Injury. *Clin. Res.* 1993, 41, 233a.
15. Morgan, et al. Role of Complement in Inflammation and Injury in the Nervous System. *Exp. Clin. Immunogenet.* 1997, 14, 19-23.
16. Vasthare, et al. Involvement of the complement System in Cerebral Ischemic and Reperfusion Injury. *FASEB J.* 1993, 7, A424.
17. Stevens, et al. Effects of Anti-C5a Antibodies on the Adult Respiratory Distress Syndrome in Septic Primates. *J. Clin. Invest.* 1986, 77, 1812-1816.
18. Nakano, et al. Myasthenia gravis: Quantitative immunocytochemical analysis of inflammatory cells and detection of complement membrane attack complex at the end-plate in 30 patients. *Neurology* 1993, 43, 1167-1172.
19. Fredrikson, et al. New Procedure for the detection of complement deficiency by ELISA. *J. Immunol. Meth.* 1993, 166, 263-270.
20. Polhill, et al. Kinetic Assessment of Alternative Complement Pathway Activity in a Hemolytic System. *J. Immunol.* 1978, 121(1), 363-370.
21. S. M. Berge et al. *J. Pharmaceutical Sciences* 1977, 66, 1 et seq.
22. Prescott, Ed., *Methods in Cell Biology*, Volume XIV, pp. 33 et seq. Academic Press: New York, 1976.
23. T. Higuchi and V. Stella, *Pro-drugs as Novel Delivery Systems*, V. 14. A.C.S. Symposium Series, 1987.
24. Gong, et al. Tubing Loops as a Model for Cardiopulmonary Bypass circuits: Both the Biomaterial and the Blood-Gas Phase Interfaces Induce Complement Activation in an in Vitro Model. *J. Clin Immunol.* 1996, 16(4), 222-229.
25. Hulett, et. al. Molecular basis of Fc receptor function. *Adv. Immunol.* 1994, 57, 1-127.

What is claimed is:

1. A method of inhibiting factor B-dependent complement activation in blood of a subject in need thereof, comprising administering to blood of the subject a therapeutically effective amount of an anti-factor B monoclonal antibody or antigen-binding fragment thereof effective to inhibit complement activation, the anti-factor B monoclonal antibody or antigen-binding fragment thereof in an in vitro assay having a greater effectiveness at preventing factor B binding to properdin-bound C3b than preventing factor B binding to free C3b; preventing the formation of Bb; reducing C3a, C5a, and C5b-9 generation; reducing C3 conversion into C3a and C3b; reducing C5 conversion into C5a and C5b; reducing the activation of neutrophils, monocytes and platelets; and inactivating cells bearing C3a and C5a receptors, wherein administration of the therapeutically effective amount of the monoclonal antibody or antigen-binding fragment thereof does not decrease factor B levels in the blood.

2. The method of claim 1, wherein the monoclonal antibody or antigen-binding fragment thereof specifically binds to factor B and factor B fragments.

3. The method of claim 1, wherein the monoclonal antibody or antigen-binding fragment thereof is recombinant, chimeric, humanized or human antibody.

4. The method of claim 1, wherein the antigen-binding fragment is selected from the group consisting of F(ab), F(ab)2, Fv and scFv.

5. The method of claim 1 wherein the complement alternative pathway is substantially inhibited.

6. The method of claim 1, wherein the complement activation is associated with inflammation in a subject.

7. The method of claim 1, wherein the complement activation is associated with a disease.

8. A method of treating disease pathologies associated with complement activation mediated by factor B in human blood, the method comprising administering to human blood a therapeutically effective amount of a monoclonal antibody or antigen-binding fragment thereof that binds to factor B present in the human blood, the anti-factor monoclonal B antibody or antigen-binding fragment thereof in an in vitro assay having a greater effectiveness at preventing factor B binding to properdin-bound C3b than preventing factor B binding to free C3b; preventing the formation of Bb; reducing C3a, C5a, and C5b-9 generation; reducing C3 conversion into C3a and C3b; reducing C5 conversion into C5a and C5b; reducing the activation of neutrophils, monocytes and platelets; and inactivating cells bearing C3a and C5a receptors, wherein administration of the therapeutically effective amount of the monoclonal antibody or antigen-binding fragment thereof does not decrease factor B levels in the blood.

9. The method of claim 8, wherein the monoclonal antibody or antigen-binding fragment thereof is recombinant, chimeric, humanized or human antibody.

10. The method of claim 8, wherein the antigen-binding fragment is selected from the group consisting of F(ab), F(ab)2, Fv and scFv.

11. The method of claim 8, wherein the complement alternative pathway is substantially inhibited.

12. The method of claim 8, wherein the complement activation is associated with inflammation in a subject.

13. A method of inhibiting complement alternative pathway activation associated with extracorporeal circulation inflammation, the method comprising;

contacting factor B in blood of a subject undergoing extra corporeal circulation with a therapeutically effective amount of a monoclonal antibody or antigen-binding fragment thereof that specifically binds to factor B, the anti-factor B monoclonal antibody or antigen-binding fragment thereof in an in vitro assay having a greater effectiveness at preventing factor B binding to properdin-bound C3b than factor B binding to free C3b, preventing the formation of Bb; reducing C3a, C5a, and C5b-9 generation in blood, reducing C3 conversion into C3a and C3b; reducing C5 conversion into C5a and C5b; reducing the activation of neutrophils, monocytes and platelets and inactivating cells bearing C3a and C5a receptors, wherein administration of the therapeutically effective amount of the monoclonal antibody or antigen-binding fragment thereof does not decrease factor B levels in the blood.

14. The method of claim 13, wherein the monoclonal antibody or antigen-binding fragment thereof is recombinant, chimeric, humanized or human antibody.

15. The method of claim 13, wherein the antigen-binding fragment is selected from the group consisting of F(ab), F(ab)2, Fv and scFv.

16. The method of claim 13, wherein the complement alternative pathway is substantially inhibited.

17. The method of claim 13, wherein complement activation is associated with inflammation in a subject.

* * * * *